(12) United States Patent
De Man et al.

(10) Patent No.: US 10,689,343 B2
(45) Date of Patent: Jun. 23, 2020

(54) INHIBITORS OF TRYPTOPHAN 2,3-DIOXYGENASE

(71) Applicant: NETHERLANDS TRANSLATIONAL RESEARCH CENTER B.V., Oss (NL)

(72) Inventors: Adrianus Petrus Antonius De Man, Hurwenen (NL); Joost Cornelis Marinus Uitdehaag, Oss (NL); Jan Gerard Sterrenburg, Renkum (NL); Joeri Johannes Petrus De Wit, Boekel (NL); Nicole Wilhelmina Cornelia Seegers, Heesch (NL); Antonius Maria Van Doornmalen, Kerkdriel (NL); Rogier Christian Buijsman, Berghem (NL); Guido Jenny Rudolf Zaman, Berghem (NL)

(73) Assignee: NETHERLANDS TRANSLATIONAL RESEARCH CENTER B.V. (NL)

(*) Notice: Subject to any disclaimer, the term of this patent is extended or adjusted under 35 U.S.C. 154(b) by 0 days.

(21) Appl. No.: 16/317,245

(22) PCT Filed: Jul. 11, 2017

(86) PCT No.: PCT/EP2017/067447
§ 371 (c)(1),
(2) Date: Jan. 11, 2019

(87) PCT Pub. No.: WO2018/011227
PCT Pub. Date: Jan. 18, 2018

(65) Prior Publication Data
US 2019/0315688 A1    Oct. 17, 2019

(30) Foreign Application Priority Data

Jul. 13, 2016   (EP) .................................... 16179348

(51) Int. Cl.
*C07D 209/18*    (2006.01)
*C07D 209/20*    (2006.01)
*C07D 401/12*    (2006.01)
*C07D 403/10*    (2006.01)
*C07D 403/12*    (2006.01)
*C07D 407/12*    (2006.01)
*C07D 413/12*    (2006.01)
*C07D 453/02*    (2006.01)
*C07D 471/04*    (2006.01)
*C07D 209/08*    (2006.01)
*C07F 5/02*      (2006.01)

(52) U.S. Cl.
CPC ......... *C07D 209/08* (2013.01); *C07D 209/18* (2013.01); *C07D 209/20* (2013.01); *C07D 401/12* (2013.01); *C07D 403/10* (2013.01); *C07D 403/12* (2013.01); *C07D 407/12* (2013.01); *C07D 413/12* (2013.01); *C07D 453/02* (2013.01); *C07D 471/04* (2013.01); *C07F 5/027* (2013.01)

(58) Field of Classification Search
CPC .. C07D 209/18; C07D 209/20; C07D 401/12; C07D 403/10; C07D 403/12; C07D 407/12; C07D 413/12; C07D 453/02; C07D 471/04
See application file for complete search history.

(56) References Cited

FOREIGN PATENT DOCUMENTS

| WO | WO2015067782 A1 | 5/2015 |
|----|-----------------|--------|
| WO | WO2015121812 A1 | 8/2015 |
| WO | WO2015140717 A1 | 9/2015 |
| WO | WO2016024233 A1 | 2/2016 |
| WO | WO2016026772 A1 | 2/2016 |
| WO | WO2016071283 A1 | 5/2016 |

(Continued)

OTHER PUBLICATIONS

Reynolds, G. P., and S. J. Pearson. "Increased brain 3-hydroxykynurenine in Huntington's disease." The Lancet 334.8669 (1989): 979-980.
Schmidt, Silvia K., et al. "Antimicrobial and immunoregulatory properties of human tryptophan 2, 3-dioxygenase." European journal of immunology 39.10 (2009): 2755-2764.
Seegers, Nicole, et al. "High-throughput fluorescence-based screening assays for tryptophan-catabolizing enzymes." Journal of biomolecular screening 19.9 (2014): 1266-1274.
Van Der Goot, Annemieke T., et al. "Delaying aging and the aging-associated decline in protein homeostasis by inhibition of tryptophan degradation." Proceedings of the National Academy of Sciences (2012): 201203083.

(Continued)

*Primary Examiner* — Laura L Stockton
(74) *Attorney, Agent, or Firm* — Mendelsohn Dunleavy, P.C.

(57) ABSTRACT

The invention relates to a compound of Formula I: Formula I, or pharmaceutically acceptable enantiomers, or salts thereof. The present invention also relates to the use of compounds of Formula (I) as selective inhibitors of tryptophan 2,3-dioxygenase. The invention also relates to the use of the compounds of Formula (I) for the treatment or prevention of cancer and central nervous system disease or disorder, either as a single agent or in combination with other therapies.

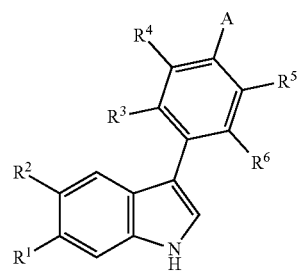

Formula I

10 Claims, No Drawings

(56) References Cited

FOREIGN PATENT DOCUMENTS

| WO | WO2016071293 A2 | 5/2016 | |
|----|-----------------|--------|---|
| WO | WO-2017/025868 A1 * | 2/2017 | ........... C07D 417/04 |

OTHER PUBLICATIONS

Vécsei, László, et al. "Kynurenines in the CNS: recent advances and new questions." Nature reviews Drug discovery 12.1 (2013): 64.

International Search Report and Written Opinion; dated Oct. 4, 2017 for PCT Application No. PCT/EP2017/067447.

Campesan, Susanna, et al. "The kynurenine pathway modulates neurodegeneration in a *Drosophila* model of Huntington's disease." Current Biology 21.11 (2011): 961-966.

Heyes, Melvyn P., et al. "Sources of the neurotoxin quinolinic acid in the brain of HIV-1-infected patients and retrovirus-infected macaques." The FASEB journal 12.10 (1998): 881-896.

Kanai, Masaaki, et al. "Tryptophan 2, 3-dioxygenase is a key modulator of physiological neurogenesis and anxiety-related behavior in mice." Molecular brain 2.1 (2009): 8.

Klockow, Jessica L., and Timothy E. Glass. "Development of a Fluorescent Chemosensor for the Detection of Kynurenine." Organic letters 15.2 (2012): 235-237.

Lu, Changyuan, Yu Lin, and Syun-Ru Yeh. "Inhibitory substrate binding site of human indoleamine 2, 3-dioxygenase." Journal of the American Chemical Society 131.36 (2009): 12866-12867.

Madge, D. J., et al. "Novel tryptophan dioxygenase inhibitors and combined tryptophan dioxygenase/5-HT reuptake inhibitors." Bioorganic & Medicinal Chemistry Letters 6.7 (1996): 857-860.

Miller, Christine L., et al. "Upregulation of the initiating step of the kynurenine pathway in postmortem anterior cingulate cortex from individuals with schizophrenia and bipolar disorder." Brain research 1073 (2006): 25-37.

Ogawa, T., et al. "Kynurenine pathway abnormalities in Parkinson's disease." Neurology 42.9 (1992) Abstract Only: 1702-1702.

Pilotte, Luc, et al. "Reversal of tumoral immune resistance by inhibition of tryptophan 2, 3-dioxygenase." Proceedings of the National Academy of Sciences 109.7 (2012): 2497-2502.

Reynolds, Gavin P., et al. "Brain quinolinic acid in Huntington's disease." Journal of neurochemistry 50.6 (1988): 1959-1968.

* cited by examiner

INHIBITORS OF TRYPTOPHAN 2,3-DIOXYGENASE

The present invention relates to substituted 3-phenyl-1H-indole derivatives as selective inhibitors of tryptophan 2,3-dioxygenase, to pharmaceutical compositions comprising these compounds and their use in therapy. In particular, the present invention relates to the use of substituted 3-phenyl-1H-indole derivatives for the treatment of cancer and central nervous system disease.

The present invention relates to substituted 3-phenyl-1H-indole compounds which modulate the activity of tryptophan 2,3-dioxygenase, in particular inhibit the activity of tryptophan 2,3-dioxygenase. Tryptophan 2,3-dioxygenase (TDO, EC 1.13.11.11) is an oxidoreductase that catalyzes the first and rate-limiting step of the kynurenine pathway of L-tryptophan degradation. L-tryptophan is an essential amino acid required for the synthesis of proteins and the production of the neurotransmitter 5-hydroxy tryptamine (serotonin) and niacin (vitamin $B_3$). Both L-tryptophan and L-tryptophan metabolites formed along the kynurenine pathway are regulators of the immune response.

TDO is mainly expressed in the liver and is induced by the stress hormone cortisol and by L-tryptophan. In addition, TDO is overexpressed in many tumors. In particular, TDO was found to be expressed in tumor samples from bladder carcinomas, melanomas, and hepatocellular carcinomas (Pilotte, L., et al., Proc. Natl. Acad. Sci. USA 109: 2497; 2012). TDO was also found to be expressed in brain, liver and colon cancer cell lines (Pilotte et al.; Opitz, C. A., et al., Nature 478: 197; 2011; Seegers, N., et al., J. Biomol. Screen. 19: 1266; 2014). Expression of TDO in cancer cells inhibited the proliferation of activated T cells by depleting L-tryptophan (Schmidt, S. K., et al., Eur. J. Immunol. 39: 2755; 2009). TDO expressed in mouse tumor cells prevented their rejection and this effect could be reverted by LM10, a selective inhibitor of TDO (Pilotte, L., et al.). The effect only occurred in immunocompetent mice and not in a immune-deficient mice strain. This suggests that overexpression of TDO in tumors can create a state of immune tolerance, and that this state can be broken with a TDO inhibitor. Mice treated with LM10 did not show any signs of toxicity in the liver or any other organs, indicating that treatment with a TDO inhibitor can be safe (Pilotte, L., et al.)

Above data provide the basis of the use TDO inhibitors as an approach for selective anti-cancer therapy.

TDO inhibitors can be applied in anti-cancer therapy as single anti-cancer agent (monotherapy) or in combination with other anti-cancer agents. TDO inhibitors may also be applied in anti-cancer therapy with other agents that activate the immune response, such as radiotherapy, or cellular therapies that attack tumor cells directly, such as natural killer cell or T cell therapies.

L-Tryptophan and metabolites formed along the kynurenine pathway play diverse role in the regulation of functions of the central nervous system (Vecsei, L., et al., Nat. Rev. Drug Discov. 12: 64; 2013). L-tryptophan is a precursor of serotonin (5-hydroxy tryptamine), while metabolites formed in the kynurenine pathway have neurotoxic activity. Increased levels of TDO protein and mRNA, and increased metabolites were found in postmortem samples of patients with schizophrenia and bipolar disorder (Miller, C. L, et al., Brain Res. 1073-1074: 25; 2006). Increased levels of metabolites have also been found in the brains of people with Huntington's disease (Reynolds, G. P., et al., J. Neurochem. 50: 1959; 1988; Reynolds, G. P., and Pearson, S. J., Lancet 2: 979; 1989), Parkinson's disease (Ogawa, T., et al., Neurology 42: 1702; 1992) and human immunodeficiency virus (HIV) associated neurocognitive disorder (AIDS dementia complex) (Heyes, M. P., et al., FASEB J., 12: 881; 1998). Mice deficient for the TDO gene showed less anxiety-related behavior and increased neurogenesis (Kanai, M., et al., Mol. Brain 2:8; 2009). Genetic inactivation of TDO in the fruit fly *Drosophila melanogaster* and in the roundworm *Caenorhabditis elegans* decreased the toxic accumulation of proteins in models of Huntington's and Parkinson's disease (Campesan, S., et al., Curr. Biol. 21: 961; 2011; van der Goot, A., et al., Proc. Natl. Acad. Sci. USA 109: 14912; 2012). Madge et al. (Bioorg. Med. Chem. Lett. 6, 857; 1996) described indole derivatives as TDO inhibitors. Dosing of rats resulted in a 2.5-fold increase of L-tryptophan, and a 1.5 times increase of serotonin levels in the cerebrospinal fluid.

Above data provide the biologic basis for the application of TDO inhibitors in the treatment of diseases of the central nervous system.

TDO inhibitors can be applied as single agent (monotherapy), or in combination with other therapeutically active agents, such as for instance, selective serotonin reuptake inhibitors (SSRIs) for treating depression.

Thus inhibiting TDO activity, thereby increasing L-tryptophan concentrations and decreasing L-tryptophan metabolite concentration is a promising way of treating diseases, disorders and other pathological conditions arising from an increased L-tryptophan degradation.

Small molecule inhibitors of TDO are currently being developed to treat or prevent pathological conditions that are dependent or induced by increased degradation of L-tryptophan or by increased formation of metabolites of L-tryptophan, such as the diseases and disorders described above. The use of small molecule inhibitors of TDO in therapy has been described.

Madge, D. J., et al. (Bioorg. Med. Chem. Lett. 6, 857; 1996) described indole derivatives with TDO inhibitory activity and combined inhibitors of TDO and serotonin uptake.

WO 2015/067782 A1 describes 4-(indol-3-yl)-pyrazole derivatives as inhibitors of TDO. WO2015/121812 A1 discloses 3(-indol-3-yl)-pyridine derivatives that modulate the TDO enzyme. WO2015/140717 A1 describes substituted indole derivatives as TDO inhibitors.

Several TDO inhibitors also inhibit the activity of indoleamine 2,3-dioxygenase (IDO1) in biochemical assays (Seegers, N., et al., J. Biomol. Screen. 19: 1266; 2014). For example, WO 2016/024233 A1, WO 2016/026772 A1, WO2016/071283 A1 and WO2016/071293 A1 describe different chemical classes with combined TDO and IDO1 inhibitory activity.

IDO1 is a structurally unrelated oxidoreductase that catalyzes the same reaction as TDO in the kynurenine pathway. IDO1 has a higher affinity ($K_M$, $T_{rp}$) for L-tryptophan (6 μM) than TDO (190 μM) (Lu, C., et al. J. Am. Chem. Soc. 131: 12866; Klockow, J. L. et al., Organic Lett. 15: 235; 2013). IDO1 is broadly expressed at sites of immune cell activity and is induced by gamma interferon. Cross-reactivity of TDO inhibitors against IDO1 can be determined in enzyme assays.

Both TDO and IDO1 contain a heme cofactor. Also cytochrome P450 enzymes (CYPs), which are enzymes involved in the metabolism of drugs in the liver and other organs, contain a heme cofactor. Inhibition of CYP activity can cause adverse drug interactions, since by inhibition of CYP, one drug may affect the metabolism and clearance of a second drug. Consequently, the second drug may accumulate to toxic levels within the body, and adjustments of dosage levels may be necessary. Cross-reactivity of TDO inhibitors against CYPs can be determined in enzyme assays.

In view of the role of TDO in (the onset of) a variety of human diseases, disorders and other pathological conditions arising from an increased L-tryptophan degradation associated with an increased activity of TDO, there is a clear need for TDO inhibitors that are potent, selective and that do not cross react with IDO1 and/or CYPs.

It is an object of the invention to provide novel TDO inhibitors. It is another object of the invention to provide novel TDO inhibitors which are selective for TDO and do not cross-react with IDO1 and/or CYP. It is yet a further objective of the present invention to provide novel, selective TDO inhibitors which have a potent cellular activity.

The present invention provides for such TDO inhibitors. In particular, the present invention provides for substituted 3-phenyl-1H-indole derivatives as potent inhibitors of TDO. The present invention provides for substituted 3-phenyl-1H-indole derivatives which selectively inhibit TDO activity, their use in therapy, either as a sole agent or in combination with other therapeutically active ingredients, as well as pharmaceutical compositions comprising such compounds and pharmaceutical carriers.

In particular, the present invention relates to the use of substituted 3-phenyl-1H-indole derivatives in the treatment and/or prevention of a diverse array of diseases, pathological conditions and disorders associated with an increased activity of TDO, including cancer and central nervous system disease or disorders.

More specifically, the present invention provides substituted 3-phenyl-1H-indole derivatives according to Formula I Formula I

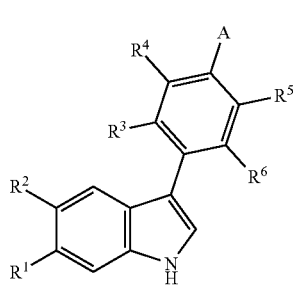

or pharmaceutically acceptable salts thereof, wherein, $R^1$ is selected from the group consisting of hydrogen or fluoro, $R^2$ is selected from the group consisting of hydrogen or fluoro,
with the proviso that when $R^1$ is fluoro, $R^2$ is hydrogen and when $R^1$ is hydrogen, $R^2$ is fluoro, $R^3$ is selected from the group consisting of hydrogen, halogen, (1-6C)alkyl or (1-6C)alkoxy, $R^4$ is selected from the group consisting of hydrogen, halogen, (1-6C)alkyl or (1-6C)alkoxy, $R^5$ is selected from the group consisting of hydrogen, halogen, (1-6C)alkyl or (1-6C)alkoxy, $R^6$ is selected from the group consisting of hydrogen, halogen, (1-6C)alkyl or (1-6C)alkoxy, A is selected from the group consisting of:

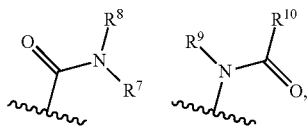

$R^7$ is selected from the group consisting of:
  a) hydrogen,
  b) hydroxy(1-6C)alkyloxy,
  c) hydroxy(1-6C)alkyl,
  d) di[(1-6C)alkyl]amino(1-6C)alkyl,
  e) aminocarbonyl(1-6C)alkyl,
  f) amino(1-6C)alkyl,
  g) (6-10C)aryl(1-6C)alkyl,
  h) (3-7C)cycloalkyl(1-6C)alkyl,
  i) (3-7C)cycloalkyl,
  j) (2-7C)heterocycloalkyl(1-6C)alkyl,
  k) (2-7C)heterocycloalkyl,
  l) (1-9C)heteroaryl(1-6C)alkyl,
  m) (1-6C)alkyl,
  n) (1-6C)alkoxycarbonyl(1-6C)alkyl,
  a) (1-6C)alkoxy(1-6C)alkyl,
  p) (1-5C)heteroaryl,
  q) (1-6C)alkyloxycarbonyl(1-6C)alkyl, $R^7$ optionally being substituted with one or more groups selected from halogen, hydroxyl, amino, cyano, hydroxy(1-6C)alkyl, di[(1-6C)alkyl]amino(1-6C)alkyl, (6-10C)aryl, (3-7C)cycloalkyl, (2-7C)heterocycloalkyl, (1-6C)alkyl, (1-6C)alkylcarbonyl, (1-6C)alkyloxycarbonyl, aminosulfonyl, (1-6C)alkylsulfonyl, (1-6C)alkylaminothiocarbonyl, (1-6C)alkylaminocarbonyl or (1-6C)alkoxy, $R^8$ is selected from the group consisting of:
  a) hydrogen,
  b) (1-6C)alkyl,
or $R^7$ and $R^8$ form, together with the N atom they are attached to, a (1-5C)heteroaryl or (2-7C)heterocycloalkyl, optionally substituted with one or more halogen, amino or hydroxy(1-6C)alkyl, $R^9$ is selected from the group consisting of:
  a) hydrogen,
  b) (1-6)alkyl), $R^{10}$ is selected from the group consisting of:
  a) hydrogen,
  b) (1-6C)alkyl,
  c) hydroxy(1-6C)alkyl,
  d) (6-10C)aryl(1-6C)alkyl,
  e) (3-7C)cycloalkyl(1-6C)alkyl,
  f) (3-7C)cycloalkyl,
  g) (2-7C)heterocycloalkyl(1-6C)alkyl,
  h) (2-7C)heterocycloalkyl,
  i) (1-6C)alkoxy(1-6C)alkyl,
  j) (1-6C)alkylthio(1-6C)alkyl,
  k) (1-6C)alkylsulfonyl(1-6C)alkyl,
  l) (1-6C)alkoxycarbonyl(1-6C)alkyl,
  m) (1-6C)alkylamino(1-6C)alkyl,
  n) (1-5C)heteroaryl(1-6C)alkyl,
  o) $N(R^{101}R^{102})$, $R^{10}$ optionally being substituted with one or more groups selected from halogen, hydroxyl, amino, cyano, (1-6C)alkyl or (2-7C)heterocycloalkyl, $R^{101}$ is selected from the group consisting of:
a) hydrogen,
b) (1-6C)alkyl,
$R^{102}$ is selected from the group consisting of:
a) hydrogen,
b) (1-6C)alkyl.

The terms as used herein refer to the following:

Halogen means fluorine, chlorine, bromine or iodine, with fluorine, chlorine or bromine being preferred halogens, fluorine or chlorine being more preferred.

(1-2C)Alkyl means an alkyl group having 1 to 2 carbon atoms, being methyl or ethyl, methyl being preferred. A methyl group may be indicated as Me or $CH_3$.

(1-3C)Alkyl means a branched or unbranched alkyl group having 1-3 carbon atoms, being methyl, ethyl, propyl or isopropyl, (1-2C)alkyl groups being preferred.

(1-4C)Alkyl means a branched or unbranched alkyl group having 1-4 carbon atoms, being methyl, ethyl, propyl, isopropyl, butyl, isobutyl, sec-butyl or tert-butyl, (1-3C) alkyl groups being preferred.

(1-5C)Alkyl means a branched or unbranched alkyl group having 1-5 carbon atoms, for example methyl, ethyl, propyl, isopropyl, butyl, isobutyl, sec-butyl, tert-butyl, pentyl and isopentyl, (1-4C)alkyl groups being preferred.

(1-6C)Alkyl means a branched or unbranched alkyl group having 1-6 carbon atoms, for example methyl, ethyl, propyl, isopropyl, butyl, tert-butyl, n-pentyl and n-hexyl. (1-5C)alkyl groups are preferred, (1-4C)alkyl being more preferred.

(1-2C)Alkoxy means an alkoxy group having 1-2 carbon atoms, the alkyl moiety having the same meaning as previously defined.

(2-4C)Alkoxy means an alkoxy group having 2-4 carbon atoms, for example ethoxy, propyloxy, butyloxy, isopropyloxy, isobutyloxy, and tertbutyloxy. Ethyloxy and propyloxy being preferred. Ethyloxy groups being more preferred.

(1-3C)Alkoxy means an alkoxy group having 1-3 carbon atoms, the alkyl moiety having the same meaning as previously defined. (1-2C)alkoxy groups are preferred.

(1-4C)Alkoxy means an alkoxy group having 1-4 carbon atoms, the alkyl moiety having the same meaning as previously defined. (1-3C)alkoxy groups are preferred, (1-2C)alkoxy groups being most preferred.

(1-5C)Alkoxy means an alkoxy group having 1-5 carbon atoms, the alkyl moiety having the same meaning as previously defined. (1-4C)alkoxy groups are preferred, (1-3C)alkoxy groups being more preferred.

(1-6C)Alkoxy means an alkoxy group having 1-6 carbon atoms, the alkyl moiety having the same meaning as previously defined. (1-5C)alkoxy groups are preferred, (1-4C)alkoxy groups being more preferred.

Hydroxy(1-6C)alkyl means an (1-6C)alkyl group having the same meaning as previously defined, substituted with a hydroxyl group Hydroxy(1-6C)alkyloxy means an oxy-group substituted with a hydroxy(1-6C)alkyl group having the same meaning as previously defined.

Hydroxy(1-6C)alkyl means an (1-6C)alkyl group having 1-6 carbon atoms with the same meaning as previously defined, substituted with a hydroxyl group.

(1-6C)Alkylamino means an amino group, monosubstituted with an alkyl group containing 1-6 carbon atoms and having the same meaning as previously defined. Preferred (1-6C)alkylamino group is methylamino.

Di[(1-6C)alkyl]amino means an amino group, disubstituted with alkyl group(s) each independently containing 1-6 carbon atoms and having the same meaning as previously defined. Preferred di[(1-6C)alkyl]amino group is dimethylamino.

Di[(1-6C)alkyl]amino(1-6C)alkyl means an alkyl group with 1-6 carbon atoms and having the same meaning as previously defined, substituted with a di[(1-6C)alkyl] amino group having the same meaning as previously defined.

Aminocarbonyl(1-6C)alkyl means an (1-6C)alkyl group as previously defined, substituted with an aminocarbonyl group.

Amino(1-6C)alkyl means an (1-6C)alkyl group as previously defined, substituted with an amino group.

(6-10C)Aryl means an aromatic hydrocarbon group having 6-10 carbon atoms, such as phenyl, naphthyl, tetrahydronaphthyl or indenyl. The preferred (6-10C)aryl group is phenyl.

(6-10C)Aryl(1-6C)alkyl means an (1-6C)alkyl group as previously defined, substituted with an (6-10C)aryl group having the same meaning as previously defined.

(3-7C)Cycloalkyl means a cycloalkyl group having 3-7 carbon atoms, being cyclopropyl, cyclobutyl, cyclopentyl, cyclohexyl or cycloheptyl. Preferred (3-7C)cycloalkyl groups are cyclohexyl, cyclopentyl, cyclobutyl or cyclopropyl, more preferred (3-7C)cycloalkyl groups are cyclobutyl and cyclopropyl.

(3-7C)Cycloalkyl(1-6C)alkyl means an (1-6C)alkyl group as previously defined, substituted with an (3-7C)cycloalkyl group having the same meaning as previously defined.

(2-7C)Heterocycloalkyl means a heterocycloalkyl group having 2-7 carbon atoms, preferably 2-5 carbon atoms, and one or two heteroatoms selected from N, O and/or S. Preferred heteroatoms are N or O. Preferred (2-7C)heterocycloalkyl groups are azetidinyl, pyrrolidinyl, piperidinyl, piperazinyl, homopiperidinyl, morpholinyl or thiomorpholinyl, more preferred (2-7C)heterocycloalkyl groups are pyrrolidinyl and piperidyl The heterocycloalkyl group may be attached via a heteroatom if feasible.

(2-7C)Heterocycloalkyl(1-6C)alkyl means an (1-6C)alkyl group as previously defined, substituted with an (2-7C) heterocycloalkyl group having the same meaning as previously defined.

(1-5C)Heteroaryl means a substituted or unsubstituted aromatic group having 5-6 ring atoms of which 1-5 carbon atoms and 1-4 heteroatoms selected from N, O and/or S. The (1-5C)heteroaryl may optionally be substituted. Examples of typical (1-5C) heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; Preferred (1-5C) heteroaryl groups are isoxazolyl, pyrazolyl, pyridyl, pyrimidyl, pyrazinyl, more preferred (1-5C)heteroaryls are isoxazolyl and pyrazolyl.

(1-9C)Heteroaryl means a substituted or unsubstituted aromatic group having 8-10 atoms of which 1-9 carbon atoms and 1-5 heteroatoms selected from N, O and/or S. The (1-9C)heteroaryl may optionally be substituted. Examples of typical (1-9C) heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, isobenzofuranyl, chromenyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinolinyl, cinnolinyl, pteridinyl, isothiazolyl, and the like. (1-5C)Heteroaryl groups are being preferred.

(1-9C)Heteroaryl(1-6C)alkyl means an (1-6C)alkyl group as previously defined, substituted with an (1-9C)heteroaryl group having the same meaning as previously defined.

(1-6C)Alkoxycarbonyl means an carbonyl group substituted with an (1-6C)alkoxy group having the same meaning as previously defined.

(1-6C)alkoxycarbonyl(1-6C)alkyl means an (1-6C)alkyl group as previously defined, substituted with an (1-6C)alkoxycarbonyl group having the same meaning as previously defined.

(1-6C)Alkoxy(1-6C)alkyl means an (1-6C)alkyl group as previously defined, substituted with an (1-6C)alkoxy group having the same meaning as previously defined.

(1-6C)Alkylcarbonyl means a carbonyl group substituted with an (1-6C)alkyl group having the same meaning as previously defined.

(1-6C)Alkyloxy means an oxy-group substituted with an (1-6C)alkoxy group having the same meaning as previously defined.

(1-6C)Alkyloxycarbonyl means a carbonyl group substituted with an (1-6C)alkyloxy group having the same meaning as previously defined.

Aminosulfonyl means a sulfonyl group substituted with an amino group.

(1-6C)Alkylsulfonyl means a sulfonyl group substituted with an (1-6C)alkyl group having the same meaning as previously defined.

(1-6C)Alkylaminocarbonyl means a carbonyl group substituted with an (1-6C)alkylamino group having the same meaning as previously defined.

(1-6C)Alkylthio means a thio-group substituted with an (1-6C)alkyl group having the same meaning as previously defined.

(1-6C)Alkylthio(1-6C)alkyl means an (1-6C)alkyl group substituted with an (1-6C)alkylthio group having the same meaning as previously defined.

(1-6C)Alkylsulfonyl(1-6C)alkyl means an (1-6C)alkyl group substituted with an (1-6C)alkylsulfonyl group having the same meaning as previously defined.

(1-6C)Alkylamino(1-6C)alkyl means an (1-6C)alkyl group substituted with an (1-6C)alkylamino group having the same meaning as previously defined.

(1-6C)Alkylaminothiocarbonyl means a thiocarbonyl group substituted with an (1-6C)alkylamino group having the same meaning as previously defined.

(1-5C)Heteroaryl(1-6C)alkyl means an (1-6C)alkyl group substituted with a (1-5C)heteroaryl group having the same meaning as previously defined.

In the above definitions with multifunctional groups, the attachment point is at the last group.

When, in the definition of a substituent, is indicated that "all of the alkyl groups" of said substituent are optionally substituted, this also includes the alkyl moiety of an alkoxy group.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds.

"Stable compound" or "stable structure" is defined as a compound or structure that is sufficiently robust to survive isolation to a useful degree of purity from a reaction mixture, and formulation into an efficacious therapeutic agent.

The term "optionally substituted" means optional substitution with the specified groups, radicals or moieties.

The compounds according to formula I of the present invention were found to inhibit TDO activity, which make them excellent candidates for use in the treatment or prevention of diseases, disorders and other pathological conditions associated with an increased TDO activity, in particular those disease, disorders and pathological conditions arising from an increased L-tryptophan degradation.

In one embodiment, the invention provides for a compound according to Formula I, wherein $R^1$ is fluoro, $R^2$ is hydrogen and $R^3$ to $R^6$ and A are as previously defined.

In another embodiment, the invention provides for a compound according to Formula I, wherein $R^3$ is selected from the group consisting of hydrogen, halogen, or (1-6C) alkyl, $R^4$ is selected from the group consisting of hydrogen, halogen, (1-6C)alkyl or (1-6C)alkoxy, $R^5$ is selected from the group consisting of hydrogen or halogen, $R^6$ is selected from the group consisting of hydrogen or halogen, more preferably wherein $R^1$ is fluoro, $R^2$ is hydrogen, $R^3$ is selected from the group consisting of hydrogen, halogen, or (1-6C)alkyl, $R^4$ is selected from the group consisting of hydrogen, halogen, (1-6C)alkyl or (1-6C)alkoxy, $R^5$ is selected from the group consisting of hydrogen or halogen, and $R^6$ is selected from the group consisting of hydrogen or halogen, In yet another embodiment, the invention provides for a compound according to Formula I, wherein $R^6$ is hydrogen, more preferably wherein $R^1$ is fluoro, $R^2$ is hydrogen and $R^6$ is hydrogen, even more preferably wherein $R^1$ is fluoro, $R^2$ is hydrogen, $R^3$ is selected from the group consisting of hydrogen, halogen, or (1-6C)alkyl, $R^4$ is selected from the group consisting of hydrogen, halogen, (1-6C)alkyl or (1-6C)alkoxy, $R^5$ is selected from the group consisting of hydrogen or halogen, and $R^6$ is hydrogen In again another embodiment, the invention provides for a compound according to Formula I, wherein $R^3$ is hydrogen, fluoro or methyl, preferably wherein $R^1$ is fluoro, $R^2$ is hydrogen, and $R^3$ is hydrogen, fluoro or methyl, more preferably wherein $R^1$ is fluoro, $R^2$ is hydrogen, $R^3$ is hydrogen, fluoro or methyl, $R^4$ is selected from the group consisting of hydrogen, halogen, (1-6C)alkyl or (1-6C) alkoxy, $R^5$ is selected from the group consisting of hydrogen or halogen, $R^6$ is selected from the group consisting of hydrogen or halogen, even more preferably wherein $R^1$ is fluoro, $R^2$ is hydrogen, $R^3$ is hydrogen, fluoro or methyl, $R^4$ is selected from the group consisting of hydrogen, halogen, (1-6C)alkyl or (1-6C)alkoxy, $R^5$ is selected from the group consisting of hydrogen or halogen, and $R^6$ is hydrogen.

In a further embodiment, the invention provides for a compound according to Formula I, wherein $R^5$ is hydrogen or fluoro, preferably wherein $R^1$ is fluoro, $R^2$ is hydrogen, and $R^5$ is hydrogen or fluoro, more preferably wherein $R^1$ is fluoro, $R^2$ is hydrogen, $R^3$ is selected from the group consisting of hydrogen, halogen, or (1-6C)alkyl, $R^4$ is selected from the group consisting of hydrogen, halogen, (1-6C)alkyl or (1-6C)alkoxy, $R^5$ is hydrogen or fluoro, and $R^6$ is selected from the group consisting of hydrogen or halogen, even more preferably wherein $R^1$ is fluoro, $R^2$ is hydrogen, $R^3$ is hydrogen, fluoro or methyl, $R^4$ is selected from the group consisting of hydrogen, halogen, (1-6C)alkyl or (1-6C) alkoxy, $R^5$ is hydrogen or fluoro and $R^6$ selected from the group consisting of hydrogen or halogen, particular preferably wherein $R^1$ is fluoro, $R^2$ is hydrogen, $R^3$ is hydrogen, fluoro or methyl, $R^4$ is selected from the group consisting of hydrogen, halogen, (1-6C)alkyl or (1-6C)alkoxy, $R^5$ is hydrogen or fluoro and $R^6$ is hydrogen.

In yet a further embodiment, the invention provides for a compound according to Formula I, wherein $R^4$ is hydrogen, fluoro, chloro or methoxy, preferably wherein $R^1$ is fluoro, $R^2$ is hydrogen, and $R^4$ is hydrogen, fluoro, chloro or methoxy, more preferably wherein $R^1$ is fluoro, $R^2$ is hydrogen, $R^3$ is selected from the group consisting of hydrogen, halogen, or (1-6C)alkyl, $R^4$ is hydrogen, fluoro, chloro or methoxy, $R^5$ is selected from the group consisting of hydrogen or halogen, and $R^6$ is selected from the group consisting of hydrogen or halogen, even more preferably wherein $R^1$ is fluoro, $R^2$ is hydrogen, $R^3$ is selected from the group consisting of hydrogen, halogen, or (1-6C)alkyl, $R^4$ is hydrogen, fluoro, chloro or methoxy, $R^5$ is selected from the group consisting of hydrogen or halogen, and $R^6$ is hydrogen, particularly preferable wherein $R^1$ is fluoro, $R^2$ is hydrogen, $R^3$ is hydrogen, fluoro or methyl, $R^4$ is hydrogen, fluoro, chloro or methoxy, $R^5$ is selected from the group consisting of hydrogen or halogen, and $R^6$ is hydrogen, more particularly preferable wherein $R^1$ is fluoro, $R^2$ is hydrogen, $R^3$ is hydrogen, fluoro or methyl, $R^4$ is hydrogen, fluoro, chloro or methoxy, $R^5$ is hydrogen or fluoro, and $R^6$ is hydrogen.

In again a further embodiment, the invention provides for a compound according to Formula I, wherein A is

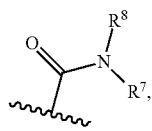

wherein $R^7$ is selected from the group consisting of hydroxy (1-6C)alkyl, amino(1-6C)alkyl, di[(1-6C)alkyl]amino(1-6C) alkyl, (2-7C)heterocycloalkyl(1-6C)alkyl, (2-7C)heterocycloalkyl, (1-6C)alkyl, $R^7$ optionally being substituted with one or more groups selected from fluoro, (1-6C)alkyl or di[(1-6C)alkyl]amino(1-6C)alkyl, and $R^8$ is hydrogen, and $R^1$ to $R^6$ may have any one of the previous definitions.

In a particularly interesting embodiment, the invention provides for compounds according to Formula I which have been demonstrated to be very potent TDO inhibitors with excellent selectivity over IDO1 and/or CYP, wherein $R^1$ is fluoro, $R^2$ is hydrogen, $R^3$ is hydrogen, fluoro or methyl, $R^4$ is hydrogen, fluoro, chloro or methoxy, preferably fluoro or chloro, $R^5$ is hydrogen or fluoro, preferably fluoro, $R^6$ is hydrogen and A is

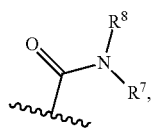

wherein $R^7$ is selected from the group consisting of hydroxy(1-6C)alkyl, amino(1-6C)alkyl, di[(1-6C)alkyl] amino(1-6C)alkyl, (2-7C)heterocycloalkyl(1-6C)alkyl, (2-7C)heterocycloalkyl, (1-6C)alkyl, $R^7$ optionally being substituted with one or more groups selected from fluoro, (1-6C)alkyl or di[(1-6C)alkyl]amino(1-6C)alkyl, and $R^8$ is hydrogen.

The invention also provides for those compounds wherein all specific definitions of $R^1$-$R^6$, A, and $R^{7-10}$ and all substituent groups in the various aspects of the inventions defined here above occur in any combination within the definition of the compound of Formula I. Suitable compounds according to the invention are the compounds according to Formula I of examples 1 to 138.

The compounds according to Formula I have an inhibitory potency on TDO in cells with an $IC_{50}$ of 2 μM or less. More preferably, the compounds according to Formula I have an inhibitory potency on TDO with an $IC_{50}$ of 500 nM or less, such as e.g. the compounds of examples 3, 4, 10, 12, 13, 14, 16, 17, 26, 27, 31, 36, 42, 43, 44, 45, 46, 47, 48, 49, 50, 51, 53, 56, 57, 59, 60, 61, 62, 63, 64, 66, 86, 87, 93, 94, 95, 97, 100, 102, 103, 104, 105, 106, 107, 109, 110, 111, 112, 113, 114, 115, 116, 117, 119, 120, 122, 127, 129, 131, 132, 136. Particularly preferred are compounds according to Formula I which have an inhibitory potency on TDO with an $IC_{50}$ of 200 nM or less, such as e.g. the compounds of examples 1, 2, 8, 15, 19, 20, 21, 23, 24, 25, 52, 54, 55, 58, 68, 69, 70, 71, 72, 73, 74, 75, 76, 77, 78, 79, 80, 81, 82, 83, 84, 118, 123, 124, 125, 133, 134, 135, 137. The compounds according to Formula I were found to have excellent cellular potency with selectivity over IDO1 and CYP.

The term $IC_{50}$ means the concentration of the test compound that is required for 50% inhibition of its maximum effect in vitro.

Inhibition of TDO activity can be measured by determining the enzymatic conversion of L-tryptophan into N-formylkynurenine (NFK) in a reaction mixture containing TDO and test compound. The formation of NFK can be detected directly by, for instance, high-performance liquid chromatography (HPLC) methods, or by intrinsic fluorescence. The formation of NFK can also be measured by using a chemical probe that reacts specifically with NFK to form a fluorescent product (Seegers, N. et al., J. Biomol. Screen. 19: 1266; 2014). Alternatively, the NFK formed in the reaction can be determined after a chemical reaction, i.e., NFK can be hydrolyzed to kynurenine, which can be measured by absorbance, fluorescence or HPLC methods (Matin, A., et al., Anal. Biochem. 349: 96; 2006).

The biological activity of TDO inhibitors can be measured by applying above detection methods to cells that are treated with test compound. Endogenous expression of TDO has been determined in a variety of cancer cell lines (Pilotte et al.; Seegers, et al.), or TDO can be expressed in cells that lack endogenous TDO by transfection of an expression vector containing TDO cDNA. For the purpose of this invention, the $IC_{50}$ is the concentration of the test compound that is required for 50% inhibition of its maximum effect in vitro, measured in a biochemical or cell based assay, such as the assays described by Seegers et al, 2014 supra. A preferred assay is the cell-based NFK GreenScreen™ assay (Seegers et al, supra), which measures the cellular inhibitory activity of compounds on TDO. For the purpose of this invention, potent cellular activity is defined as having an $IC_{50}$ value of 2 μM or less, measured in a cell-based assay such as described by Seegers et al, 2014 supra. Unless expressed differently, all $IC_{50}$ values relating to the inhibitory potency on TDO are based on cell-based inhibitory activity of the TDO inhibitors. Selectivity over IDO1 is defined as having a biochemical inhibitory activity on IDO1 with $IC_{50}$ values of 25 μM or more, measured in a biochemical assay such as e.g. the NFK GreenScreen™ assay. Selectivity over CYP is defined as having a biochemical inhibitory activity on CYPs with $IC_{50}$ values of 5 µM or more, measured in a biochemical assay such as e.g. the P450-Glo CYP3A4 luciferin isopropylacetal (Luc-IP) assay (Promega, Madison, Wis., USA, Cat. No. V9920).

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I may contain both a basic moiety, such as, but not limited to a pyridine or imidazole, and an acidic moiety, zwitterions ("inner salts") may be formed and are included within the term "salt(s)" as used herein. Pharmaceutically acceptable (i.e., non-toxic, physiologically acceptable) salts are preferred. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartrates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, J. of Pharm. Sci. (1977) 66(1) 1-19; P. Gould, Int. J. Pharm. (1986) 33 201-21 7; Anderson et al, The Practice of Medicinal Chemistry (1996), Academic Press, New York; and in The Orange Book (Food & Drug Administration, Washington, D.C. on their website).

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, tert-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The compounds of Formula I may have the ability to crystallize in more than one form, a characteristic known as polymorphism, and it is understood that such polymorphic forms ("polymorphs") are within the scope of Formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula I contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula I may be atropisomers (e.g. substituted biaryls) and are considered as part of this invention. Enantiomers can also be separated by use of a chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the compounds according to the invention.

The compounds having Formula I or the pharmaceutically accepted salts may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature.

Substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herein below, by substituting an appropriate isotopically labeled reagent for a non-isotopically labeled reagent.

In a second aspect of the invention, the compounds according to Formula I or a pharmaceutically acceptable salt thereof can be used as a medicament in therapy. More in particular, the compounds according to Formula I or a pharmaceutically acceptable salt thereof can be used for the treatment of diseases or conditions caused by, or associated with increased activity of TDO, in particular diseases or disorders caused by, or associated with increased tryptophan metabolism.

In particular, the compounds of Formula I or their salts, and pharmaceutical compositions thereof can be used to treat cancer.

In another embodiment, the compounds of the present invention, their salts and pharmaceutical compositions thereof can be used to increase the efficacy of one or more other anti-cancer agents, e.g., chemotherapeutic agents, vaccines, antibodies, or cell therapies.

In again another aspect, the compounds of the present invention, their salts and pharmaceutical compositions thereof can be used to treat or prevent the negative effects of tryptophan metabolites, which are related to increased activity of TDO, in neuropsychiatric disease, such as schizophrenia and bipolar disorder.

In yet a further embodiment, the compounds of the present invention, their salts and pharmaceutical compositions thereof can be used to treat or prevent neurodegenerative disease, such as Parkinson's or Huntington's disease.

A further aspect of the invention resides in the use of a compound of Formula 1, pharmaceutically acceptable salts and pharmaceutical compositions thereof in the treatment of diseases, disorders and pathological conditions caused by or associated with overexpression or over-activity of the TDO protein, in particular diseases, disorders and conditions wherein an increased tryptophan degradation plays a prominent role.

Included herein are methods of treatment and/or pharmaceutical compositions in which at least one compound of Formula I or a pharmaceutically acceptable salt thereof is administered as a single agent or in combination with at least one other therapeutically active agent. The other therapeutically active agent can be a chemotherapeutic agent, an antibody, engineered immune cells or an active polypeptide.

Thus, in one embodiment, the invention concerns a compound of Formula I or salt thereof in combination with one or more other drug(s).

In a third aspect, the invention further provides a pharmaceutical composition, which comprises a compound of Formula I and salts thereof, and one or more pharmaceutically acceptable carriers, diluents, or excipients. The carrier (s), diluent(s) or excipient(s) must be acceptable in the sense of being compatible with the other ingredients of the formulation and not deleterious to the recipient thereof.

Mixed with such pharmaceutically acceptable auxiliaries, e.g. as described in the standard reference, Gennaro, A. R. et al., Remington: The Science and Practice of Pharmacy (20th Edition, Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

Pharmaceutical compositions of the present invention may be presented in unit dose forms containing a predetermined amount of active ingredient per unit dose. Such a unit may contain, for example, 5 μg to 1 g, preferably 1 mg to 700 mg, more preferably 5 mg to 100 mg of a compound of the Formula I, depending on the condition being treated, the route of administration and the age, weight and condition of the patient. Such unit doses may therefore be administered more than once a day. Preferred unit dosage compositions are those containing a daily dose or sub-dose (for administration more than once a day), as here in above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, sublingual, subcutaneous, local or parenteral (including intravenous and intramuscular) route, and the like, all in unit dosage forms for administration. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

The compound of the present invention can also be administered as a protein-drug conjugate. The compound can be covalently bound, optionally with a linker molecule to a peptide or protein, such as a binding protein for example an antibody. Using this approach, the conjugate can be delivered to the target tissue. Methods to prepare such conjugates are well known to those skilled in the art.

The compound of the present invention can also be administered as a (bio)polymeric nanoparticulate-drug system (Park, W. et al., Nanomed. Nanobiotechnol. 7: 494-508; 2015). The compound can be covalently bound, optionally with a linker molecule to the nanoparticulate system for example, but not limited to, a polymeric micelle. Using this approach, the nanoparticulate can be delivered to the target tissue. Methods to prepare such nanoparticulates are well known to those skilled in the art.

It will be appreciated that when the compound of the present invention is administered in combination with other therapeutic agents normally administered by the inhaled, intravenous, oral or intranasal route, that the resultant pharmaceutical composition may be administered by the same routes.

A therapeutically effective amount of a compound of the present invention will depend upon a number of factors including, for example, the age and weight of the animal, the precise condition requiring treatment and its severity, the particular compound having Formula I, the nature of the formulation, and the route of administration, and will ultimately be at the discretion of the attendant physician or veterinarian. However, an effective amount of a compound of Formula I for the treatment of diseases or conditions associated with inappropriate TDO protein, will generally be in the range of 5 µg to 100 mg/kg body weight of recipient (mammal) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula I per se.

In general parenteral administration requires lower dosages than other methods of administration which are more dependent upon absorption. However, a dosage for humans preferably contains 0.0001-25 mg of a compound of Formula I or pharmaceutically acceptable salts thereof per kg body weight. The desired dose may be presented as one dose or as multiple sub-doses administered at appropriate intervals throughout the day, or, in case of female recipients, as doses to be administered at appropriate daily intervals throughout the menstrual cycle. The dosage, as well as the regimen of administration, may differ between a female and a male recipient.

The present invention also relates to a pharmaceutical composition comprising a compound of Formula I or pharmaceutically acceptable salt thereof in a mixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition comprising at least one compound of Formula I or pharmaceutically acceptable salts thereof in combination with at least one other therapeutically active agent.

For the treatment of cancer a compound of Formula I may be combined with one or more anticancer agents. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved.

The 3-phenyl-1H-indole derivatives of the present invention can be prepared by methods well known in the art of organic chemistry. See, for example, J. March, '*Advanced Organic Chemistry*' $4^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts '*Protective Groups in Organic Synthesis*' $3^{rd}$ Edition, John Wiley and Sons, 1999. The protective groups are optionally removed at a convenient subsequent stage using methods well known in the art.

The products of the reactions are optionally isolated and purified, if desired, using conventional techniques, including but not limited to, filtration, distillation, crystallization, chromatography and the like. Such materials are optionally characterized using conventional means, including physical constants and spectral data.

Substituted 3-phenyl-1H-indole containing compounds of Formula I, wherein $R^1$ to $R^x$ have the previously defined meanings, can be prepared by the general synthetic route shown in scheme I.

Scheme I

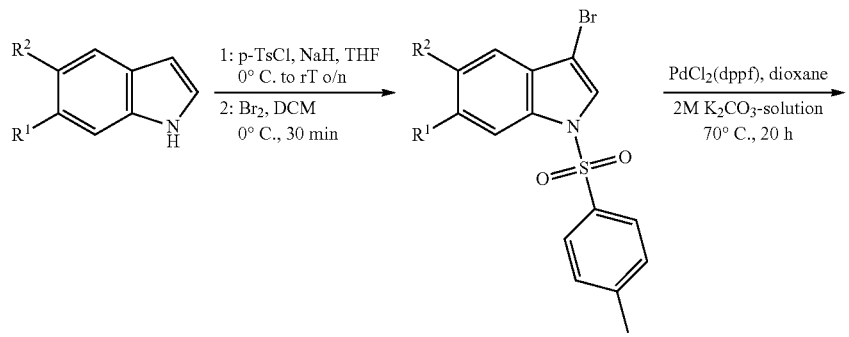

I

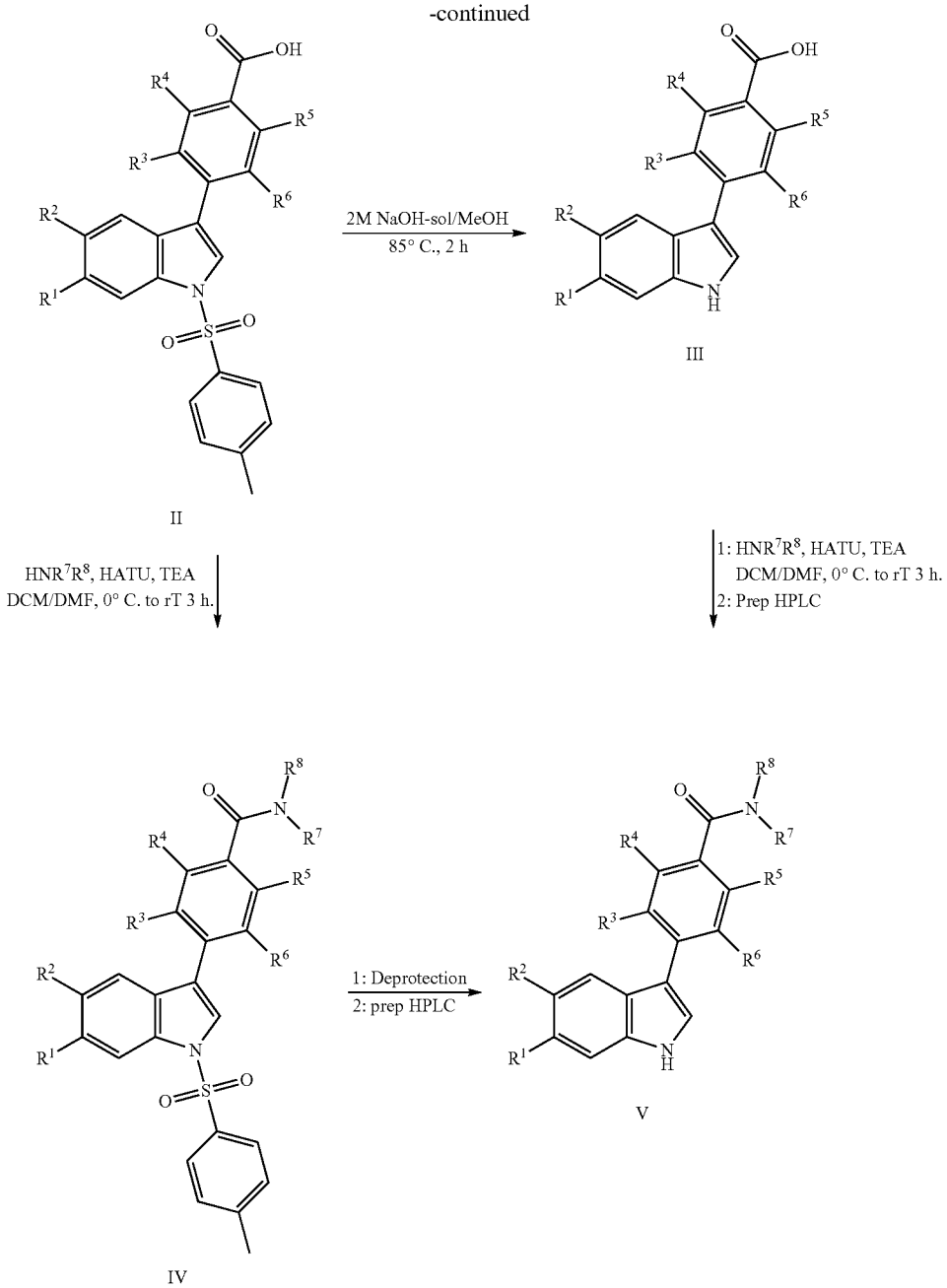

Benzylsulfonyl or tosyl-protected 3-bromoindoles (I) can be prepared from commercially available indoles in a two-step synthesis starting with deprotonation of the indole with bases like NaH, LiHMDS or BEMP in an appropriate solvent such as THF or DMF and subsequent reaction with tosylchloride or benzylsulfonylchloride. After bromination of the sulfonyl-protected indoles using bromine in dichloromethane, derivatives I were obtained. Substituted phenyl-carboxylates can be introduced by reaction of derivatives I and their corresponding phenyl-substituted 4-(4,4,5,5-tetramethyl-1,3,2-dioxaborolan-2-yl)benzoic acids or substituted 4-boronobenzoic acids in the presence of a suitable palladium catalyst system, for example 1,1'-bis(dipehylphosphino)ferrocene palladium(II)chloride or tetrakis(triphenyl-phosphine)palladium(0) in the presence of an inorganic base such as potassium carbonate, cesium carbonate or potassium phosphate in a suitable solvent system like dioxane and water to generate derivatives II. Deprotection of derivatives II can be accomplished using 2M NaOH-solution in methanol at reflux temperatures for 2 h to obtain derivatives III. Introduction of $N(R^7R^8)$ can be performed using standard coupling reactions well known in the art to obtain derivatives IV or V. Derivatives IV can be deprotected using 2M NaOH-solution in methanol at reflux temperatures or reaction with 1M TBAF-solution in THF to obtain derivatives V. Finally purification using preparative HPLC delivered compounds of formula (I).

Substituted 3-phenyl-1H-indole containing compounds of Formula I, wherein $R^1$ to $R^x$ have the previously defined meanings, can also be prepared by the general synthetic route shown in scheme II.

Scheme II

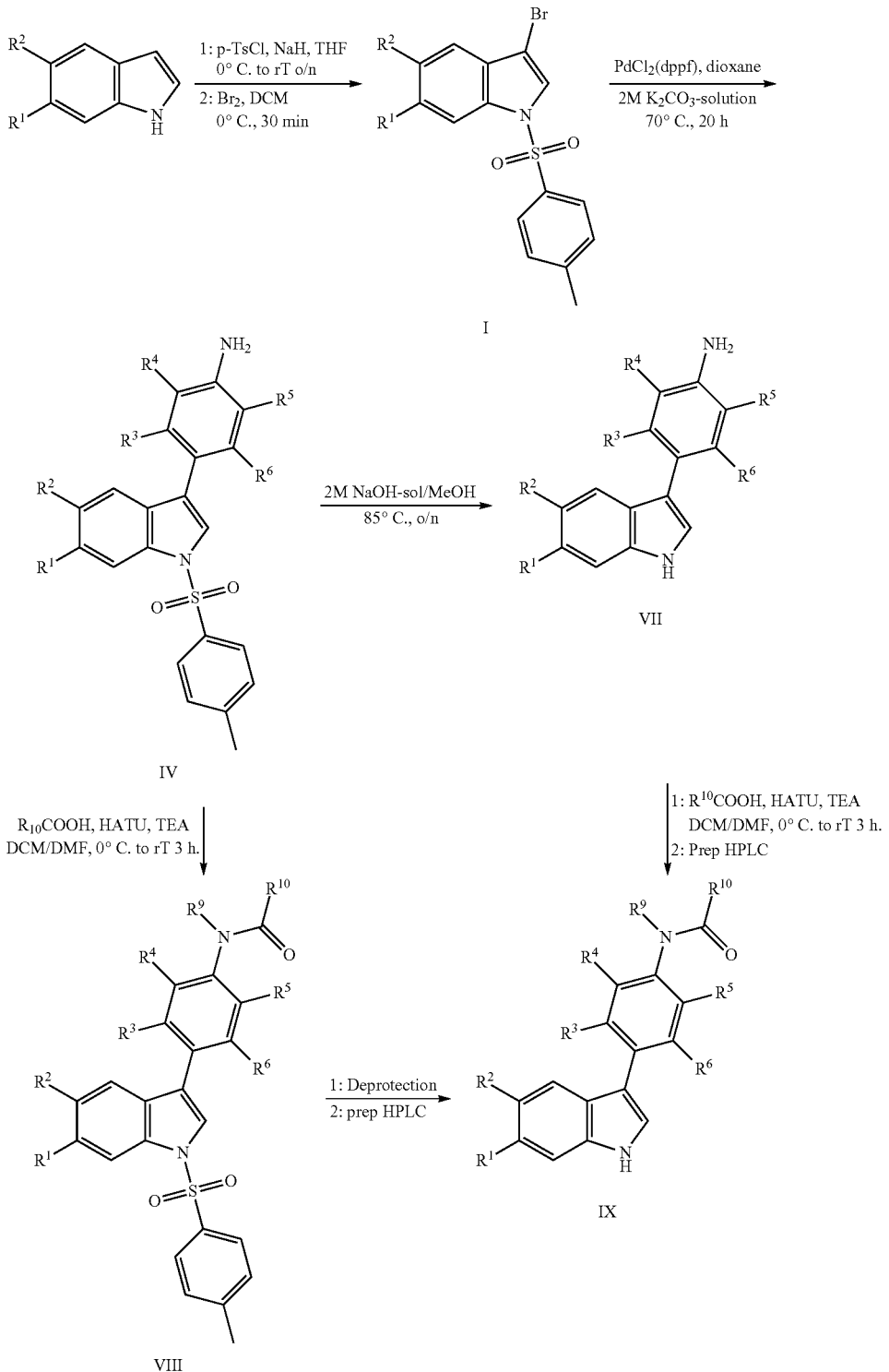

Tosyl-protected 3-bromoindoles (I) can be prepared as described in scheme I. Substituted phenylcarboxylates can be introduced by reaction of derivatives I and their corresponding phenyl-substituted 4-(4,4,5,5-tetramethyl-1,3,2-dioxaborolan-2-yl)anilines or substituted (4-aminophenyl) boronic acids in the presence of a suitable palladium catalyst system, for example 1,1'-bis(dipehylphosphino)ferrocene palladium(II)chloride or tetrakis-(triphenylphosphine)palladium(0) in the presence of an inorganic base such as potassium carbonate, cesium carbonate or potassium phosphate in a suitable solvent system like dioxane and water to generate derivatives VI. Deprotection of derivatives VI can be accomplished using 2M NaOH-solution in methanol at reflux temperatures to obtain derivatives VII. Introduction of $R^{10}COOH$ can be performed using standard coupling reactions well known in the art to obtain derivatives VIII or IX. Derivatives VIII can be deprotected using 2M NaOH-solution in methanol at reflux temperatures or reaction with 1M TBAF-solution in THF at reflux temperatures to obtain derivatives IX. Finally purification using preparative HPLC delivered compounds of formula (I).

Alternatively Substituted 3-phenyl-1H-indole containing compounds of Formula I, wherein $R^1$ to $R^x$ have the previously defined meanings, can also be prepared by the general synthetic route shown in scheme III.

in the presence of a suitable palladium catalyst system, for example 1,1'-bis(dipehylphosphino)ferrocene palladium(II) chloride or tetrakis(triphenylphosphine)palladium(0) in the presence of an inorganic base such as potassium carbonate, cesium carbonate or potassium phosphate in a suitable solvent system like dioxane and water to generate derivatives X. Deprotection of derivatives X can be accomplished using 2M NaOH-solution in methanol at reflux temperatures to obtain derivatives XI. Finally purification using preparative HPLC delivered compounds of Formula (I).

The invention is illustrated by the following examples.

EXAMPLES

The following examples are illustrative embodiments of the invention, not limiting the scope of the invention in any way. Reagents are either commercially available or are prepared according to procedures known in the literature.

Method LCMS (A)

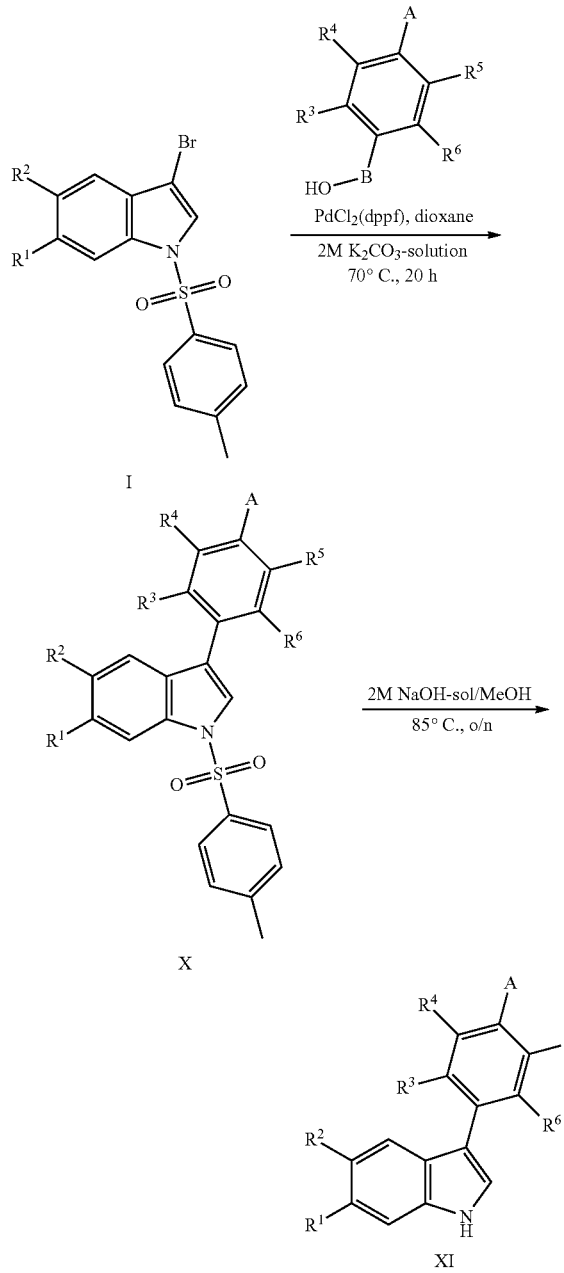

| Method name | NTRC_C18_Short.M | |
|---|---|---|
| Column | Waters XTerra C18-MS, 50 × 4.6 mm ID, 2.5 μm | |
| Flow | 0.5 ml/min. | |
| Temperature | 40° C. | |
| Detector DAD | 210, 254, 280 nm | |
| Detector MSD | API-ES | |
| MSD signal | 1 | 2 |
| Mode | Scan | Scan |
| Polarity | Positive | Negative |
| Mass Range | 100-1000 m/z | 100-1000 m/z |
| Fragmentor | 70 | 70 |
| Cycle Time | 50% | 50% |
| Sample preparation | N/A | |
| Concentration | 1 mg/ml in MeOH or ACN | |
| Injection volume | 1.0 μl | |

| | A | B |
|---|---|---|
| Eluent Time [min] | % 0.1% Formic Acid | % 0.05% Formic Acid in Acetonitrile |
| 0 | 90 | 10 |
| 0.3 | 90 | 10 |
| 7.0 | 10 | 90 |
| 7.1 | 90 | 10 |
| 10.0 | 90 | 10 |

| Post time | 0.2 min | Stop time | 10 min |
|---|---|---|---|

Method LCMS (B)

| Method LCMS (B) Method name | NTRC_C18.M | |
|---|---|---|
| Column | Waters XTerra C18-MS, 50 × 4.6 mm ID, 2.5 μm | |
| Flow | 0.5 ml/min. | |
| Temperature | 40° C. | |
| Detector DAD | 210, 254, 280 nm | |
| Detector MSD | API-ES | |
| MSD signal | 1 | 2 |
| Mode | Scan | Scan |
| Polarity | Positive | Negative |
| Mass Range | 100-1000 m/z | 100-1000 m/z |
| Fragmentor | 70 | 70 |
| Cycle Time | 50% | 50% |

Substituted 3-phenyl-1H-indole (X) can be prepared starting from derivatives I and their corresponding boronic acids

| Sample preparation | N/A |
|---|---|
| Concentration | 1 mg/ml in MeOH or ACN |
| Injection volume | 1.0 μl |

| Eluent Time [min] | A % 0.1% Formic Acid | B % 0.05% Formic Acid in Acetonitrile |
|---|---|---|
| 0 | 90 | 10 |
| 1 | 90 | 10 |
| 22.0 | 10 | 90 |
| 22.1 | 90 | 10 |
| 30.0 | 90 | 10 |

| Post time | 0.2 min | Stop time | 30 min |
|---|---|---|---|

Method Preparative HPLC

| LC System | Waters Prep System |
|---|---|
| Column | Phenomenex Luna, C18(2) 100 A, 150 mm × 21.2 mm, 5 μm |
| Column Temp | 20° C. |
| Sample(s) | 10-50 mg |
| Autosamp. Temp | 20° C. |
| Injection volume | 500-950 μL |
| Flow | 15 ml/min |
| Eluent | A = MilliQ + MeCN (9/1) B = Acetonitrile C = 0.1N TFA/water |

| Gradient | time (min) | % A | % B | % C |
|---|---|---|---|---|
| | 0 | 97 | 0 | 3 |
| | 20 | 37 | 60 | 3 |
| | 25 | 37 | 60 | 3 |
| | 25.1 | 97 | 0 | 3 |
| | 30 | 97 | 0 | 3 |

| UV detection | Photo Diode Array |
|---|---|

The following abbreviations are used throughout the application with respect to chemical terminology:

HATU O-(7-Azabenzotriazol-1-yl)-1,1,3,3-tetramethyluroniumhexafluorophosphate
DCM Dichloromethane
THF Tetrahydrofuran
DMF N,N-Dimethylformamide
DMA N,N-Dimethylacetamide
HOBt 1-Hydroxybenzotriazole
TBAF Tetrabutylammonium fluoride
EDCl.HCl N-(3-Dimethylaminopropyl)-N'-ethylcarbodiimide hydrochloride
DiPEA N,N-Diisopropylethylamine
HPLC High Performance Liquid Chromatography
LCMS Liquid Chromatography with Mass Spectrometry detection
HCl Hydrogen chloride
NaHCO$_3$ Sodium bicarbonate
Na$_2$S$_2$O$_3$ Sodium thiosulfate
PdCl$_2$(dppf) [1,1'-Bis(diphenylphosphino)ferrocene]dichloropalladium(II), complex with dichloromethane
K$_2$CO$_3$ Potassium carbonate
Boc tert-Butyloxycarbonyl
Cbz Benzyloxycarbonyl The names of the final products in the examples are generated using Accelrys Draw (version 4.1).

Intermediate 1

3-Bromo-6-fluoro-1-(p-tolylsulfonyl)indole (a) 6-Fluoro-1-(p-tolylsulfonyl)indole To a cold (4° C.) solution of 6-fluoroindole (5 g, 32.45 mmol) in anhydrous THF (50 ml) was added sodium hydride (60% dispersion in mineral oil, 1.56 g, 39.93 mmol) and the reaction mixture was stirred for 20 min. p-Toluenesulfonylchloride (7.42 g, 39.93 mmol) was added, and the reaction mixture was stirred at room temperature overnight. The reaction was quenched by adding a saturated NaHCO$_3$-solution (500 ml) and the mixture was subsequently extracted with ethyl acetate. The combined organic layers were washed with water, brine, dried over sodium sulfate, filtered and evaporated. The residue was triturated with ethyl acetate/heptane and the solid formed was filtered, washed with heptane and dried under vacuum to give 5.76 g of the title compound (yield 61.4%).

(b) 3-Bromo-6-fluoro-1-(p-tolylsulfonyl)indole

To a cold (0° C.) solution of 6-fluoro-1-(p-tolylsulfonyl)indole (16.1 g, 55.6 mmol) in dichloromethane (166 ml) was added dropwise over a period of 45 min a solution of bromine (3.13 ml, 61.2 mmol) in dichloromethane (40 ml). The reaction mixture was stirred at 0° C. for 30 min. then saturated aqueous Na$_2$S$_2$O$_3$ (150 ml) was added and the mixture was stirred at room temperature for 1 h. The organic layer was separated and the aqueous layer was extracted with dichloromethane (2×). The combined organic layers were subsequently washed with 5% NaHCO$_3$-solution, and brine, dried over sodium sulfate, filtered, and concentrated. The residue was triturated with heptane/ethyl acetate 80/20 v/v % (100 ml) for 45 min at 60° C. The white solid was filtered and dried under vacuum to give 20.01 g (92%) of the title compound.

Intermediate 2

1-(Benzenesulfonyl)-3-bromo-5-fluoro-indole

This compound was prepared in an analogous manner as described for Intermediate 1, starting from 5-fluoroindole and benzenesulfonyl chloride to afford the title compound (1.4 g, quant.).

Intermediate 3

4-(6-Fluoro-1H-indol-3-yl)benzoic Acid (a) 4-[6-Fluoro-1-(p-tolylsulfonyl)indol-3-yl]benzoic Acid 3-bromo-6-fluoro-1-(p-tolylsulfonyl)indole (3.9 g, 10.59 mmol) and 4-(4,4,5,5-tetramethyl-1,3,2-dioxaborolan-2-yl)benzoic acid (3.94 g, 15.88 mmol) were dissolved in dioxane (60 mL) and a solution of 2N K$_2$CO$_3$ in water (26.5 ml) was added. The reaction mixture was purged with nitrogen for 5 min after which PdCl$_2$(dppf) (424 mg, 0.52 mmol) was added. The reaction mixture was stirred for 20 h at 70° C. under nitrogen atmosphere. The mixture was diluted with ethyl acetate and filtered over Decalite™. The filtrate was collected and the pH was adjusted to pH 3 by addition of 2N aq. HCl-solution. The organic layer was separated and washed with water and brine, dried over sodium sulfate, filtered and evaporated to dryness to give crude product. The crude product was triturated with acetonitrile at 50° C. for 15 min. After cooling, the precipitate was filtered and washed with acetonitrile, dried under vacuum to give 3.7 g of the title compound (91%) as a light brown solid.

(b) 4-(6-Fluoro-1H-indol-3-yl)benzoic Acid

4-[6-Fluoro-1-(p-tolylsulfonyl)indol-3-yl]benzoic acid (3.74 g, 14.6 mmol) was dissolved in a mixture of methanol (20 ml) and a 2M NaOH-solution in water (17.8 ml, 73 mmol) and the mixture was stirred at 85° C. for 2 h. After cooling to room temperature, the pH was adjusted to pH 3 by addition of 2M HCl-solution. The suspension obtained was stirred for 30 min at room temperature and filtered. The precipitate was washed with water and dried under vacuum to give 2.3 g (62%) of the title compound.

Intermediate 4

4-(5-Fluoro-1H-indol-3-yl)benzoic Acid

This compound was prepared in an analogous manner as described for Intermediate 3, starting from 1-(benzenesulfonyl)-3-bromo-5-fluoro-indole (Intermediate 2) to afford the title compound (172 mg, 92%).

Intermediate 5

4-(6-Fluoro-1H-indol-3-yl)aniline (a) 4-[6-Fluoro-1-(p-tolylsulfonyl)indol-3-yl]aniline 3-Bromo-6-fluoro-1-(p-tolylsulfonyl)indole (500 mg, 1.36 mmol) and 4-(4,4,5,5-(313 mg, 1.43 mmol) were dissolved in dioxane (10.5 ml) and solution of 2N $K_2CO_3$ in water (3.4 ml, 6.75 mmol) was added. The mixture was purged with nitrogen for 5 min after which $PdCl_2(dppf)$ (111 mg, 0.14 mmol) was added. The mixture was stirred under $N_2$-atmosphere for another 3 min. The reaction mixture was heated for 30 min at 120° C. under microwave radiation. The mixture was diluted with dichloromethane and filtered over Decalite™. The filtrate was evaporated and the crude product was purified by column chromatography (heptane to ethyl acetate=10/0 to 0/10 v/v %) to afford 451 mg of 4-[6-fluoro-1-(p-tolylsulfonyl)indol-3-yl]aniline (87% yield).

(b) 4-(6-Fluoro-1H-indol-3-yl)aniline

4-[6-Fluoro-1-(p-tolylsulfonyl)indol-3-yl]aniline (413 mg, 1.09 mmol) was dissolved in methanol (27 ml) and a 2N NaOH-solution in water (2.7 ml, 5.42 mmol) was added. The reaction mixture was refluxed o/n. The mixture was diluted by addition of water and extracted with dichloromethane (3×). The combined organic layers were washed with water, dried over sodium sulfate, filtered and evaporated. The crude product was purified by column chromatography (heptane to ethyl acetate=10/0 to 1/1 v/v %) to afford 215 mg of the title compound (87% yield).

Intermediate 6

2-Chloro-4-(6-fluoro-1H-indol-3-yl)benzoic Acid

This compound was prepared in an analogous manner as described for Intermediate 3, starting from 3-bromo-6-fluoro-1-(p-tolylsulfonyl)indole (Intermediate 1) and 2-chloro-4-(4,4,5,5-tetramethyl-1,3,2-dioxaborolan-2-yl) benzoic acid to afford the title compound (132 mg, quantitative).

Intermediate 7

2,6-Difluoro-4-(6-fluoro-1H-indol-3-yl)benzoic Acid

This compound was prepared in an analogous manner as described for Intermediate 3, starting from 3-bromo-6-fluoro-1-(p-tolylsulfonyl)indole (Intermediate 1) and 4-borono-2,6-difluoro-benzoic acid to afford the title compound (60 mg, 94%).

Intermediate 8

4-(6-Fluoro-1H-indol-3-yl)-2-methoxy-benzoic Acid

This compound was prepared in an analogous manner as described for Intermediate 3, starting from 3-bromo-6-fluoro-1-(p-tolylsulfonyl)indole (Intermediate 1) and 3-methoxy-4-methoxycarbonylphenylboronic acid pinacol ester to afford the title compound (200 mg, 95%).

Intermediate 9

2-Fluoro-4-(6-fluoro-1H-indol-3-yl)benzoic Acid

This compound was prepared in an analogous manner as described for Intermediate 3, starting from 3-bromo-6-fluoro-1-(p-tolylsulfonyl)indole (Intermediate 1) and 4-borono-2-fluoro-benzoic acid to afford the title compound (34 mg, 35%).

Intermediate 10

4-(6-Fluoro-1H-indol-3-yl)-3-methyl-benzoic Acid

This compound was prepared in an analogous manner as described for Intermediate 3, starting from 3-bromo-6-fluoro-1-(p-tolylsulfonyl)indole (Intermediate 1) and 4-borono-3-methyl-benzoic acid to afford the title compound (58 mg, 77%).

Example 1

N-[2-(dimethylamino)-1-methyl-ethyl]-4-(6-fluoro-1H-indol-3-yl)benzamide

To a cold solution (0° C.) of 4-(6-fluoro-1H-indol-3-yl) benzoic acid (Intermediate 3, 30 mg, 0.09 mmol) and N,N-dimethylpropane-1,2-diamine (18.4 mg, 0.27 mmol) in DCM/DMF=4/1 v/v % (1.5 ml) was added triethylamine (38.1 µl, 0.18 mmol) and HATU (41 mg, 0.11 mmol), after which the reaction mixture was allowed to warm to room temperature and stirred for 3 h. The reaction mixture was diluted with 5 ml DCM and washed subsequently with water, aq. 5% $NaHCO_3$ and brine. The organic layer was separated by filtration over a PE filter and concentrated in vacuo. Purification was performed using preparative HPLC to afford the title compound (10.4 mg, 32%). Data: LCMS (B) $R_t$: 6.896 min; m/z 340.2 (M+H)+.

Example 2

4-(6-Fluoro-1H-indol-3-yl)-N-isopropyl-benzamide

This compound was prepared from Intermediate 3 and isopropylamine according to the procedure described in Example 1. Purification was performed using preparative HPLC to afford the title compound (3 mg, 11%). Data: LCMS (B) $R_t$: 10.296 min; m/z 297.1 (M+H)+.

Example 3

4-(6-Fluoro-1H-indol-3-yl)-N-[(1S)-1-(hydroxymethyl)-2-methyl-propyl]benzamide To a cold solution (0° C.) of 4-[6-fluoro-1-(p-tolylsulfonyl)indol-3-yl]benzoic acid (Intermediate 3-a, 35 mg, 0.094 mmol) and (2S)-2-amino-3-methyl-butan-1-ol (10 mg, 0.1 mmol) in DCM/DMF=4/1 v/v % (1.5 ml) was added triethylamine (36 µl, 0.26 mmol) and HATU (35 mg, 0.086 mmol), after which the reaction mixture was allowed to warm to room temperature and stirred for 3 h. The reaction mixture was diluted with DCM (5 ml) and subsequently washed with water, aq. 5% NaHCO$_3$ and brine. The organic layer was separated by filtration over a PE filter and concentrated in vacuo. The crude product was purified by column chromatography (heptane to ethyl acetate=10/0 to 0/10 v/v %) to afford 4-[6-fluoro-1-(p-tolylsulfonyl)indol-3-yl]-N-[(1S)-1-(hydroxymethyl)-2-methyl-propyl]benzamide: 35 mg (64.5% yield). The purified compound was dissolved in THF (5 ml) and 1M TBAF in THF (350 µl, 0.35 mmol) was added to the reaction mixture. After heating under reflux for 2 h, the reaction mixture was concentrated in vacuo. Purification was performed using preparative HPLC to afford the title compound (2.6 mg, 9%). Data: LCMS (B) R$_t$: 10.675 min; m/z 341.2 (M+H)$^+$.

Example 4

N-[4-(6-Fluoro-1H-indol-3-yl)phenyl]acetamide

3-Bromo-6-fluoro-1-(p-tolylsulfonyl)indole (Intermediate 1, 56 mg, 0.15 mmol and N-[4-(4,4,5,5-tetramethyl-1,3,2-dioxaborolan-2-yl)phenyl]acetamide (49 mg, 0.19 mmol) were dissolved in 1,4-dioxane (1 ml) and transferred in a microwave flask. A solution of 2M K$_2$CO$_3$ in water (0.333 ml) was added and the reaction mixture was stirred under N$_2$-atmosphere for 5 min. PdCl$_2$(dppf) (12 mg, 0.015 mmol) was subsequently added and the reaction mixture was stirred under N$_2$-atmosphere for another 3 min. The reaction mixture was heated for 30 min at 120° C. under microwave radiation. Reaction mixture was then diluted with DCM and filtered over Decalite™ in a PE-filter. The organic layer is was concentrated in vacuo and the resulting crude product was purified by column chromatography (heptane/ethyl acetate=1/1 v/v %) to afford N-[4-[6-fluoro-1-(p-tolylsulfonyl)indol-3-yl]phenyl]acetamide: 59 mg (95% yield).

Deprotection was performed using 2M NaOH-solution in water/methanol at 85° C. for 3 h. Purification was performed using preparative HPLC to afford the title compound (8 mg, 22%). Data: LCMS (B) R$_t$: 10.147 min; m/z 269.2 (M+H)$^+$.

Example 5

1-[4-(6-Fluoro-1H-indol-3-yl)phenyl]-3-methyl-urea

This compound was prepared from Intermediate 1 and 1-methyl-3-[4-(4,4,5,5-tetramethyl-1,3,2-dioxaborolan-2-yl)phenyl]urea according to the procedure described in Example 4. Purification was performed using preparative HPLC to afford the title compound (10 mg, 25%). Data: LCMS (B) R$_t$: 9.719 min; m/z 284.2 (M+H)$^+$.

Example 6

1-Ethyl-3-[4-(6-fluoro-1H-indol-3-yl)phenyl]urea

This compound was prepared from Intermediate 1 and 1-ethyl-3-[4-(4,4,5,5-tetramethyl-1,3,2-dioxaborolan-2-yl)phenyl]urea according to the procedure described in Example 4. Purification was performed using preparative HPLC to afford the title compound (23 mg, 55%). Data: LCMS (B) R$_t$: 10.666 min; m/z 298.2 (M+H)$^+$.

Example 7

3-[4-(6-Fluoro-1H-indol-3-yl)phenyl]-1,1-dimethyl-urea

This compound was prepared from Intermediate 1 and 1,1-dimethyl-3-[4-(4,4,5,5-tetramethyl-1,3,2-dioxaborolan-2-yl)phenyl]urea according to the procedure described in Example 4. Purification was performed using preparative HPLC to afford the title compound (12 mg, 27%). Data: LCMS (B) R$_t$: 10.482 min; m/z 298.2 (M+H)$^+$.

Example 8

N-[3-(dimethylamino)propyl]-4-(6-fluoro-1H-indol-3-yl)benzamide

This compound was prepared from Intermediate 3-a and N,N-dimethylpropane-1,3-diamine according to the procedure described in Example 3. Purification was performed using preparative HPLC to afford the title compound (3 mg, 10%). Data: LCMS (B) R$_t$: 12.949 min; m/z 359.1 (M+H)$^+$.

Example 9

N-[(3,3-difluorocyclobutyl)methyl]-4-(6-fluoro-1H-indol-3-yl)benzamide

This compound was prepared from Intermediate 3-a and (3,3-difluorocyclobutyl)-methanamine hydrochloride according to the procedure described in Example 3. Purification was performed using preparative HPLC to afford the title compound (16 mg, 52%). Data: LCMS (B) R$_t$: 12.823 min; m/z 359.2 (M+H)$^+$.

Example 10

4-(6-Fluoro-1H-indol-3-yl)-N-(2-hydroxyethyl)benzamide

This compound was prepared from Intermediate 3-a and 2-aminoethanol according to the procedure described in Example 3. Purification was performed using preparative HPLC to afford the title compound (5 mg, 19%). Data: LCMS (B) R$_t$: 8.625 min; m/z 299.1 (M+H)$^+$.

Example 12

N-(1-cyanocyclopropyl)-4-(6-fluoro-1H-indol-3-yl)benzamide

This compound was prepared from Intermediate 3-a and 1-aminocyclopropane-carbonitrile hydrochloride according to the procedure described in Example 3. Purification was performed using preparative HPLC to afford the title compound (35 mg, 58%). Data: LCMS (B) R$_t$: 10.934 min; m/z 320.1 (M+H)$^+$.

Example 13

4-(6-Fluoro-1H-indol-3-yl)-N-(2-hydroxy-2-methyl-propyl)benzamide

This compound was prepared from Intermediate 3-a and 1-amino-2-methyl-propan-2-ol according to the procedure

Example 14

4-(6-fluoro-1H-indol-3-yl)-N-[(1R)-2-hydroxy-1-methyl-ethyl]benzamide

This compound was prepared from Intermediate 3-a and (2R)-2-aminopropan-1-ol according to the procedure described in Example 3. Purification was performed using preparative HPLC to afford the title compound (7 mg, 25%). Data: LCMS (B) $R_t$: 9.262 min; m/z 313.1 (M+H)$^+$.

Example 15

4-(6-fluoro-1H-indol-3-yl)-N-[(1S)-2-hydroxy-1-methyl-ethyl]benzamide

This compound was prepared from Intermediate 3-a and (2S)-2-aminopropan-1-ol according to the procedure described in Example 3. Purification was performed using preparative HPLC to afford the title compound (7 mg, 27%). Data: LCMS (B) $R_t$: 9.305 min; m/z 313.1 (M+H)$^+$.

Example 16

4-(6-fluoro-1H-indol-3-yl)-N-[(1R)-2-hydroxy-1-phenyl-ethyl]benzamide

This compound was prepared from Intermediate 3-a and (2R)-2-amino-2-phenyl-ethanol according to the procedure described in Example 3. Purification was performed using preparative HPLC to afford the title compound (10 mg, 31%). Data: LCMS (B) $R_t$: 11.516 min; m/z 375.1 (M+H)$^+$.

Example 17

4-(6-Fluoro-1H-indol-3-yl)-N-[(1R)-2-methoxy-1-methyl-ethyl]benzamide

This compound was prepared from Intermediate 3-a and (2R)-1-methoxypropan-2-amine according to the procedure described in Example 3. Purification was performed using preparative HPLC to afford the title compound (8.7 mg, 32%). Data: LCMS (B) $R_t$: 10.893 min; M/z 327.1 (M+H)$^+$.

Example 18

Methyl (2R)-2-[[4-(6-fluoro-1H-indol-3-yl)benzoyl]amino]propanoate

This compound was prepared from Intermediate 3-a and methyl (2R)-2-aminopropanoate hydrochloride according to the procedure described in Example 3. Purification was performed using preparative HPLC to afford the title compound (0.7 mg, 2%). Data: LCMS (A) $R_t$: 5.639 min; m/z 341.1 (M+H)$^+$.

Example 19

4-(6-Fluoro-1H-indol-3-yl)-N-[(3S)-3-piperidyl]benzamide

This compound was prepared from Intermediate 3 and tert-butyl (3S)-3-amino-piperidine-1-carboxylate according to the procedure described in Example 1. Purification was performed, after Boc-deprotection, using preparative HPLC to afford the title compound (7 mg, 38%). Data: LCMS (A) $R_t$: 4.221 min; m/z 338.2 (M+H)$^+$.

Example 20

4-(6-Fluoro-1H-indol-3-yl)-N-[(3S)-quinuclidin-3-yl]benzamide

This compound was prepared from Intermediate 3 and (S)-(−)-3-aminoquinuclidine dihydrochloride according to the procedure described in Example 1. Purification was performed using preparative HPLC to afford the title compound (3.5 mg, 11%). Data: LCMS (B) $R_t$: 6.930 min; m/z 364.1 (M+H)$^+$.

Example 21

4-(6-Fluoro-1H-indol-3-yl)-N-(2-hydroxy-1-methyl-propyl)benzamide

This compound was prepared from Intermediate 3 and 2-amino-3-butanol according to the procedure described in Example 1. Purification was performed using preparative HPLC to afford the title compound (5.8 mg, 20%). Data: LCMS (B) $R_t$: 8.859 min; m/z 327.2 (M+H)$^+$.

Example 22

4-(6-Fluoro-1H-indol-3-yl)-N-(1-methylbutyl)benzamide

This compound was prepared from Intermediate 3 and 2-aminopentane according to the procedure described in Example 1. Purification was performed using preparative HPLC to afford the title compound (14 mg, 48%). Data: LCMS (B) $R_t$: 11.689 min; m/z 325.2 (M+H)$^+$.

Example 23

N-[2-(diethylamino)-1-methyl-ethyl]-4-(6-fluoro-1H-indol-3-yl)benzamide

This compound was prepared from Intermediate 3 and N1,N1-diethylpropane-1,2-diamine according to the procedure described in Example 1. Purification was performed using preparative HPLC to afford the title compound (14 mg, 42%). Data: LCMS (B) $R_t$: 7.146 min; m/z 368.2 (M+H)$^+$.

Example 24

4-(6-Fluoro-1H-indol-3-yl)-N-(1-methyl-4-piperidyl)benzamide

This compound was prepared from Intermediate 3 and 4-amino-1-methylpiperidine according to the procedure described in Example 1. Purification was performed using preparative HPLC to afford the title compound (7.3 mg, 19%). Data: LCMS (B) $R_t$: 6.744 min; m/z 352.2 (M+H)$^+$.

Example 25

4-(6-Fluoro-1H-indol-3-yl)-N-(1-methyl-3-piperidyl)benzamide

This compound was prepared from Intermediate 3 and 3-amino-1-methylpiperidine dihydrochloride according to the procedure described in Example 1. Purification was performed using preparative HPLC to afford the title compound (14 mg, 36%). Data: LCMS (B) $R_t$: 6.933 min; m/z 352.2 $(M+H)^+$.

Example 26

4-(6-Fluoro-1H-indol-3-yl)-N-(oxetan-3-yl)benzamide

This compound was prepared from Intermediate 3 and 3-oxetanamine hydrochloride according to the procedure described in Example 1. Purification was performed using preparative HPLC to afford the title compound (2.5 mg, 7.3%). Data: LCMS (B) $R_t$: 8.745 min; m/z 311.1 $(M+H)^+$.

Example 27

N-[4-(6-fluoro-1H-indol-3-yl)phenyl]-2-methoxy-acetamide

Methoxyacetic acid (10 µL, 0.131 mmol) was dissolved in DMF (1 ml). HATU (38 mg, 0.1 mmol) and N,N-diisopropylethylamine (35 µl, 0.25 mmol) were added and the mixture was stirred for 10 min at room temperature. 4-[6-Fluoro-1-(p-tolylsulfonyl)indol-3-yl]aniline (Intermediate 5-a, 40 mg, 0.1 mmol) was added and the mixture was stirred at room temperature o/n. The mixture was subsequently washed with a solution of 5% $NaHCO_3$ and a 5% citric acid solution. The organic layer was separated from the water layer by filtering over a PE-filter. The organic layer was concentrated in vacuo and the crude product was dissolved in THF (3 ml). To this solution an 1M TBAF solution (0.5 ml, 0.5 mmol) was added and the reaction mixture was heated under reflux for 30 min. The reaction mixture was allowed to cool to room temperate and subsequently concentrated in vacuo. Purification was performed using preparative HPLC to afford the title compound (12.8 mg, 42.9%). Data: LCMS (B) $R_t$: 11.065 min; m/z 299.1 $(M+H)^+$.

Example 28

2-Cyclopropyl-N-[4-(6-fluoro-1H-indol-3-yl)phenyl]acetamide

This compound was prepared from Intermediate 5-a and cyclopropylacetic acid according to the procedure described in Example 27. Purification was performed using preparative HPLC to afford the title compound (16.9 mg, 54.8%). Data: LCMS (B) $R_t$: 12.471 min; m/z 309.2 $(M+H)^+$.

Example 29

2-(Ethylamino)-N-[4-(6-fluoro-1H-indol-3-yl)phenyl]acetamide

This compound was prepared from Intermediate 5-a and Boc-N-ethyl-glycine according to the procedure described in Example 27. Purification was performed, after Boc-deprotection, using preparative HPLC to afford the title compound (7.9 mg, 25.3%). Data: LCMS (B) $R_t$: 7.293 min; m/z 312.2 $(M+H)^+$.

Example 30

N-[4-(6-fluoro-1H-indol-3-yl)phenyl]-2-(oxetan-3-yl)acetamide

This compound was prepared from Intermediate 5-a and 2-(oxetan-3-yl)acetic acid according to the procedure described in Example 27. Purification was performed using preparative HPLC to afford the title compound (15.1 mg, 46.5%). Data: LCMS (B) $R_t$: 10.651 min; m/z 325.2 $(M+H)^+$.

Example 31

N-[4-(6-fluoro-1H-indol-3-yl)phenyl]-2-methylsulfanyl-acetamide

This compound was prepared from Intermediate 5-a and (methylthio)acetic acid according to the procedure described in Example 27. Purification was performed using preparative HPLC to afford the title compound (14.8 mg, 47.1%). Data: LCMS (B) $R_t$: 11.790 min; m/z 315.1 $(M+H)^+$.

Example 32

2-Cyano-N-[4-(6-fluoro-1H-indol-3-yl)phenyl]acetamide

This compound was prepared from Intermediate 5 and 2-cyanoacetic acid according to the procedure described in Example 1. Purification was performed using preparative HPLC to afford the title compound (23 mg, 93%). Data: LCMS (B) $R_t$: 10.524 min; m/z 294.1 $(M+H)^+$.

Example 33

N-[4-(6-fluoro-1H-indol-3-yl)phenyl]-3-methoxy-2-methyl-propanamide

This compound was prepared from Intermediate 5 and 3-methoxy-2-methyl-propanoic acid according to the procedure described in Example 1. Purification was performed using preparative HPLC to afford the title compound (8.4 mg, 31%). Data: LCMS (B) $R_t$: 11.476 min; m/z 327.2 $(M+H)^+$.

Example 34

(3S)—N-[4-(6-fluoro-1H-indol-3-yl)phenyl]-3-hydroxy-butanamide

This compound was prepared from Intermediate 5 and (3S)-3-hydroxybutanoic acid according to the procedure described in Example 1. Purification was performed using preparative HPLC to afford the title compound (17.4 mg, 66%). Data: LCMS (B) $R_t$: 9.655 min; m/z 313.1 $(M+H)^+$.

Example 35

N-[4-(6-fluoro-1H-indol-3-yl)phenyl]-3-hydroxy-3-methyl-butanamide

This compound was prepared from Intermediate 5 and 3-hydroxy-3-methyl-butanoic acid according to the procedure described in Example 1. Purification was performed using preparative HPLC to afford the title compound (9.6 mg, 35%). Data: LCMS (B) $R_t$: 10.577 min; m/z 327.1 (M+H)$^+$.

Example 36

4-(6-Fluoro-1H-indol-3-yl)-N-[(3R)-3-piperidyl]benzamide

This compound was prepared from Intermediate 3 and (R)-(−)-3-amino-1-Boc-piperidine according to the procedure described in Example 1. Purification was performed, after Boc-deprotection, using preparative HPLC to afford the title compound (1 mg, 5%). Data: LCMS (B) $R_t$: 7.458 min; m/z 338.1 (M+H)$^+$.

Example 37

4-(5-Fluoro-1H-indol-3-yl)-N-[(1R)-2-hydroxy-1-methyl-ethyl]benzamide

This compound was prepared from Intermediate 4 and (2R)-2-aminopropan-1-ol according to the procedure described in Example 1. Purification was performed using preparative HPLC to afford the title compound (10.1 mg, 32%). Data: LCMS (B) $R_t$: 9.309 min; m/z 313.1 (M+H)$^+$.

Example 38

N-[3-(dimethylamino)propyl]-4-(5-fluoro-1H-indol-3-yl)benzamide

This compound was prepared from Intermediate 4 and N,N-dimethyl-1,3-propanediamine according to the procedure described in Example 1. Purification was performed using preparative HPLC to afford the title compound (13.3 mg, 39%). Data: LCMS (B) $R_t$: 7.155 min; m/z 340.2 (M+H)$^+$.

Example 39

4-(5-Fluoro-1H-indol-3-yl)-N-(2,2,2-trifluoroethyl)benzamide

This compound was prepared from Intermediate 4 and 2,2,2-trifluoroethylamine according to the procedure described in Example 1. Purification was performed using preparative HPLC to afford the title compound (16.7 mg, 50%). Data: LCMS (B) $R_t$: 12.523 min; m/z 337.1 (M+H)$^+$.

Example 40

4-(5-Fluoro-1H-indol-3-yl)-N-[(1S)-2-hydroxy-1-methyl-ethyl]benzamide

This compound was prepared from Intermediate 4 and (2S)-2-aminopropan-1-ol according to the procedure described in Example 1. Purification was performed using preparative HPLC to afford the title compound (9.5 mg, 30%). Data: LCMS (B) $R_t$: 9.308 min; m/z 313.1 (M+H)$^+$.

Example 41

4-(5-Fluoro-1H-indol-3-yl)-N-[(3S)-3-piperidyl]benzamide

This compound was prepared from Intermediate 4 and (S)-3-amino-1-Boc-piperidine according to the procedure described in Example 1. Purification was performed, after Boc-deprotection, using preparative HPLC to afford the title compound (18.1 mg, 34%). Data: LCMS (B) $R_t$: 7.364 min; m/z 338.1 (M+H)$^+$.

Example 42

4-(6-Fluoro-1H-indol-3-yl)-N-[[(3R)-3-piperidyl]methyl]benzamide

This compound was prepared from Intermediate 3 and (S)-Boc-3-(aminomethyl)piperidine according to the procedure described in Example 1. Purification was performed, after Boc-deprotection, using preparative HPLC to afford the title compound (19.7 mg, 33%). Data: LCMS (B) $R_t$: 7.513 min; m/z 352.2 (M+H)$^+$.

Example 43

4-(6-Fluoro-1H-indol-3-yl)-N-[(3S,4R)-3-m ethoxy-4-piperidyl]benzamide

This compound was prepared from Intermediate 3 and (3S,4R)-4-amino-1-Boc-3-methoxy-piperidine according to the procedure described in Example 1. Purification was performed, after Boc-deprotection, using preparative HPLC to afford the title compound (12.2 mg, 66%). Data: LCMS (B) $R_t$: 7.550 min; m/z 368.2 (M+H)$^+$.

Example 44

4-(6-Fluoro-1H-indol-3-yl)-N-tetrahydropyran-4-yl-benzamide

This compound was prepared from Intermediate 3 and 4-aminotetrahydropyran hydrochloride according to the procedure described in Example 1. Purification was performed using preparative HPLC to afford the title compound (29 mg, 57%). Data: LCMS (B) $R_t$: 10.526 min; m/z 339.1 (M+H)$^+$.

Example 45

4-(6-Fluoro-1H-indol-3-yl)-N-[(1S)-1-([1,2,4]triazolo[4,3-a]pyridin-3-yl)ethyl]benzamide This compound was prepared from Intermediate 3 and (1S)-1-[1,2,4]triazolo[4,3-a]pyridin-3-ylethanamine dihydrochloride according to the procedure described in Example 1. Purification was performed using preparative HPLC to afford the title compound (33 mg, 55%). Data: LCMS (B) $R_t$: 9.972 min; m/z 400.1 (M+H)$^+$.

Example 46

4-(6-Fluoro-1H-indol-3-yl)-N-[2-(1-piperidyl)ethyl]benzamide

This compound was prepared from Intermediate 3 and 2-(1-piperidyl)ethanamine according to the procedure described in Example 1. Purification was performed using

Example 47

4-(6-Fluoro-1H-indol-3-yl)-N-(8-methyl-8-azabicyclo[3.2.1]octan-3-yl)benzamide

This compound was prepared from Intermediate 3 and 8-methyl-8-azabicyclo[3.2.1]octan-3-amine dihydrochloride according to the procedure described in Example 1. Purification was performed using preparative HPLC to afford the title compound (11 mg, 26%). Data: LCMS (B) $R_t$: 7.581 min; m/z 378.2 $(M+H)^+$.

Example 48

4-(6-Fluoro-1H-indol-3-yl)-N-[2-hydroxy-1-(hydroxymethyl)-1-methyl-ethyl]benzamide This compound was prepared from Intermediate 3 and 2-amino-2-methyl-1,3-propanediol according to the procedure described in Example 1. Purification was performed using preparative HPLC to afford the title compound (8.9 mg, 23%). Data: LCMS (B) $R_t$: 9.252 min; m/z 343.1 $(M+H)^+$.

Example 49

N-[(1S)-1,2-dimethylpropyl]-4-(6-fluoro-1H-indol-3-yl)benzamide

This compound was prepared from Intermediate 3 and (S)-3-methyl-2-butylamine according to the procedure described in Example 1. Purification was performed using preparative HPLC to afford the title compound (16.9 mg, 47%). Data: LCMS (B) $R_t$: 13.773 min; m/z 325.1 $(M+H)^+$.

Example 50

4-(6-Fluoro-1H-indol-3-yl)-N-[(1R,2R)-2-hydroxycyclohexyl]benzamide

This compound was prepared from Intermediate 3 and trans-2-aminocyclohexanol hydrochloride according to the procedure described in Example 1. Purification was performed using preparative HPLC to afford the title compound (16.2 mg, 42%). Data: LCMS (B) $R_t$: 11.060 min; m/z 353.1 $(M+H)^+$.

Example 51

2-Chloro-4-(6-fluoro-1H-indol-3-yl)-N-[(1R)-2-hydroxy-1-methyl-ethyl]benzamide

This compound was prepared from Intermediate 6 and (2R)-2-aminopropan-1-ol according to the procedure described in Example 1. Purification was performed using preparative HPLC to afford the title compound (16 mg, 54%). Data: LCMS (B) $R_t$: 10.085 min; m/z 347.1 $(M+H)^+$ (chloride pattern).

Example 52

2-Chloro-N-[3-(dimethylamino)propyl]-4-(6-fluoro-1H-indol-3-yl)benzamide

This compound was prepared from Intermediate 6 and N,N-dimethylpropane-1,3-diamine according to the procedure described in Example 1. Purification was performed using preparative HPLC to afford the title compound (16 mg, 50%). Data: LCMS (B) $R_t$: 7.585 min; M/Z 374.1 $(M+H)^+$ (chloride pattern).

Example 53

2-Chloro-4-(6-fluoro-1H-indol-3-yl)-N-(2,2,2-trifluoroethyl)benzamide

This compound was prepared from Intermediate 6 and 2,2,2-trifluoroethanamine according to the procedure described in Example 1. Purification was performed using preparative HPLC to afford the title compound (16 mg, 50%). Data: LCMS (B) $R_t$: 13.430 min; m/z 371.0 $(M+H)^+$ (chloride pattern).

Example 54

2-Chloro-4-(6-fluoro-1H-indol-3-yl)-N-[(1S)-2-hydroxy-1-methyl-ethyl]benzamide

This compound was prepared from Intermediate 6 and (2S)-2-aminopropan-1-ol according to the procedure described in Example 1. Purification was performed using preparative HPLC to afford the title compound (11.5 mg, 38%). Data: LCMS (B) $R_t$: 10.085 min; m/z 347.1 $(M+H)^+$ (chloride pattern).

Example 55

2-Chloro-4-(6-fluoro-1H-indol-3-yl)-N-[(3S)-3-piperidyl]benzamide

This compound was prepared from Intermediate 6 and tert-butyl (3S)-3-aminopiperidine-1-carboxylate according to the procedure described in Example 1. Purification was performed, after Boc-deprotection, using preparative HPLC to afford the title compound (26 mg, 58%). Data: LCMS (B) $R_t$: 7.770 min; m/z 372.1 $(M+H)^+$ (chloride pattern).

Example 56

2,6-Difluoro-4-(6-fluoro-1H-indol-3-yl)-N-[(1R)-2-hydroxy-1-methyl-ethyl]benzamide This compound was prepared from Intermediate 7 and (2R)-2-aminopropan-1-ol according to the procedure described in Example 1. Purification was performed using preparative HPLC to afford the title compound (17 mg, 57%). Data: LCMS (B) $R_t$: 9.932 min; m/z 349.1 $(M+H)^+$.

Example 57

2,6-Difluoro-4-(6-fluoro-1H-indol-3-yl)-N-(2,2,2-trifluoroethyl)benzamide

This compound was prepared from Intermediate 7 and 2,2,2-trifluoroethanamine according to the procedure described in Example 1. Purification was performed using preparative HPLC to afford the title compound (3 mg, 7%). Data: LCMS (B) $R_t$: 13.318 min; m/z 373.1 $(M+H)^+$.

Example 58

2,6-Difluoro-4-(6-fluoro-1H-indol-3-yl)-N-[(3S)-3-piperidyl]benzamide

This compound was prepared from Intermediate 7 and tert-butyl (3S)-3-aminopiperidine-1-carboxylate according to the procedure described in Example 1. Purification was performed, after Boc-deprotection, using preparative HPLC to afford the title compound (10.5 mg, 25%). Data: LCMS (B) $R_t$: 7.627 min; m/z 374.1 (M+H)$^+$.

Example 59

N-[3-(dimethylamino)propyl]-2,6-difluoro-4-(6-fluoro-1H-indol-3-yl)benzamide

This compound was prepared from Intermediate 7 and N,N-dimethylpropane-1,3-diamine according to the procedure described in Example 1. Purification was performed using preparative HPLC to afford the title compound (23 mg, 41%). Data: LCMS (B) $R_t$: 7.456 min; m/z 376.2 (M+H)$^+$.

Example 60

2,6-Difluoro-4-(6-fluoro-1H-indol-3-yl)-N-[(1S)-2-hydroxy-1-methyl-ethyl]benzamide This compound was prepared from Intermediate 7 and (2S)-2-aminopropan-1-ol according to the procedure described in Example 1. Purification was performed using preparative HPLC to afford the title compound (7 mg, 12%). Data: LCMS (B) $R_t$: 9.939 min; m/z 349.1 (M+H)$^+$.

Example 61

N-(cis-4-aminocyclohexyl)-4-(6-fluoro-1H-indol-3-yl)benzamide

This compound was prepared from Intermediate 3 and 1-N-Boc-cis-1,4-cyclohexyldiamine according to the procedure described in Example 1. Purification was performed, after Boc-deprotection, using preparative HPLC to afford the title compound (7.3 mg, 16.9%). Data: LCMS (B) $R_t$: 7.326 min; m/z 352.2 (M+H)$^+$.

Example 62

4-(6-Fluoro-1H-indol-3-yl)-N-[(1-hydroxycyclobutyl)methyl]benzamide

This compound was prepared from Intermediate 3 and 1-(aminomethyl)cyclobutanol according to the procedure described in Example 1. Purification was performed using preparative HPLC to afford the title compound (14 mg, 38%). Data: LCMS (B) $R_t$: 10.626 min; m/z 339.1 (M+H)$^+$.

Example 63

4-(6-Fluoro-1H-indol-3-yl)-N-[(4-hydroxy-1-methyl-4-piperidyl)methyl]benzamide

This compound was prepared from Intermediate 3 and 4-(aminomethyl)-1-methyl-piperidin-4-ol according to the procedure described in Example 1. Purification was performed using preparative HPLC to afford the title compound (18.5 mg, 44%). Data: LCMS (B) $R_t$: 7.072 min; m/z 382.2 (M+H)$^+$.

Example 64

4-(6-Fluoro-1H-indol-3-yl)-N-[(1R,5S)-3-oxabicyclo[3.1.0]hexan-6-yl]benzamide

This compound was prepared from Intermediate 3 and (1R,5S)-3-oxabicyclo[3.1.0]-hexan-6-amine according to the procedure described in Example 1. Purification was performed using preparative HPLC to afford the title compound (15.2 mg, 41%). Data: LCMS (B) $R_t$: 10.314 min; m/z 337.1 (M+H)$^+$.

Example 65

4-(6-Fluoro-1H-indol-3-yl)-N-[2-hydroxy-1-(hydroxymethyl)ethoxy]benzamide

This compound was prepared from Intermediate 3 and 0-(2,2-dimethyl-1,3-dioxan-5-yl)hydroxylamine according to the procedure described in Example 1. Purification was performed after dimethylketal-deprotection using preparative HPLC to afford the title compound (10.7 mg, 32%). Data: LCMS (B) $R_t$: 8.658 min; m/z 345.1 (M+H)$^+$.

Example 66

N-[(2S)-2,3-dihydroxypropoxy]-4-(6-fluoro-1H-indol-3-yl)benzamide

This compound was prepared from Intermediate 3 and 0-[[(4S)-2,2-dimethyl-1,3-dioxolan-4-yl]methyl]hydroxylamine according to the procedure described in Example 1. Purification was performed after dimethylketal-deprotection using preparative HPLC to afford the title compound (11.6 mg, 35%). Data: LCMS (B) $R_t$: 8.363 min; m/z 345.1 (M+H)$^+$.

Example 67

N-[(2R)-2,3-dihydroxypropoxy]-4-(6-fluoro-1H-indol-3-yl)benzamide

This compound was prepared from Intermediate 3 and 0-[[(4R)-2,2-dimethyl-1,3-dioxolan-4-yl]methyl]hydroxylamine according to the procedure described in Example 1. Purification was performed after dimethylketal-deprotection using preparative HPLC to afford the title compound (8.26 mg, 24%). Data: LCMS (B) $R_t$: 8.365 min; m/z 345.1 (M+H)$^+$.

Example 68

2-Chloro-4-(6-fluoro-1H-indol-3-yl)-N-(1-methyl-3-piperidyl)benzamide

This compound was prepared from Intermediate 6 and 1-methylpiperidin-3-amine dihydrochloride according to the procedure described in Example 1. Purification was performed using preparative HPLC to afford the title compound (11 mg, 33%). Data: LCMS (B) $R_t$: 7.956 min; m/z 386.1 (M+H)$^+$ (chloride pattern).

Example 69

2-Chloro-4-(6-fluoro-1H-indol-3-yl)-N-(1-methyl-4-piperidyl)benzamide

This compound was prepared from Intermediate 6 and 1-methylpiperidin-4-amine according to the procedure described in Example 1. Purification was performed using preparative HPLC to afford the title compound (11.6 mg, 35%). Data: LCMS (B) $R_t$: 7.695 min; m/z 386.1 (M+H)$^+$ (chloride pattern).

Example 70

2-Chloro-4-(6-fluoro-1H-indol-3-yl)-N-(2-pyrrolidin-1-ylethyl)benzamide

This compound was prepared from Intermediate 6 and 2-(1-piperidyl)ethanamine according to the procedure described in Example 1. Purification was performed using preparative HPLC to afford the title compound (22.3 mg, 65%). Data: LCMS (B) $R_t$: 8.141 min; m/z 386.1 (M+H)$^+$ (chloride pattern).

Example 71

N-(2-aminopropyl)-2-chloro-4-(6-fluoro-1H-indol-3-yl)benzamide

This compound was prepared from Intermediate 6 and tert-butyl N-(2-amino-1-methyl-ethyl)carbamate hydrochloride according to the procedure described in Example 1. Purification was performed, after Boc-deprotection, using preparative HPLC to afford the title compound (16 mg, 54%). Data: LCMS (B) $R_t$: 7.497 min; m/z 346.1 (M+H)$^+$ (chloride pattern).

Example 72

2-Chloro-4-(6-fluoro-1H-indol-3-yl)-N-[3-(4-methylpiperazin-1-yl)propyl]benzamide This compound was prepared from Intermediate 6 and 3-(4-methylpiperazin-1-yl)propan-1-amine according to the procedure described in Example 1. Purification was performed using preparative HPLC to afford the title compound (8.2 mg, 22%). Data: LCMS (B) $R_t$: 6.794 min; m/z 429.1 (M+H)$^+$ (chloride pattern).

Example 73

2-Chloro-N-[2-(diethylamino)-1-methyl-ethyl]-4-(6-fluoro-1H-indol-3-yl)benzamide This compound was prepared from Intermediate 6 and N1,N1-diethylpropane-1,2-diamine according to the procedure described in Example 1. Purification was performed using preparative HPLC to afford the title compound (20 mg, 58%). Data: LCMS (B) $R_t$: 8.342 min; m/z 402.1 (M+H)$^+$ (chloride pattern).

Example 74

4-(6-Fluoro-1H-indol-3-yl)-N-[(3S,4R)-3-fluoro-4-piperidyl]benzamide

This compound was prepared from Intermediate 3 and (3S,4R)-tert-butyl 4-amino-3-fluoropiperidine-1-carboxylate according to the procedure described in Example 1. Purification was performed, after Boc-deprotection, using preparative HPLC to afford the title compound (30 mg, 52%). Data: LCMS (B) $R_t$: 7.294 min; m/z 356.1 (M+H)$^+$.

Example 75

4-(6-Fluoro-1H-indol-3-yl)-2-methoxy-N-[(3S)-3-piperidyl]benzamide

This compound was prepared from Intermediate 8 and (S)-3-amino-1-Boc-piperidine according to the procedure described in Example 1. Purification was performed, after Boc-deprotection, using preparative HPLC to afford the title compound (16.6 mg, 41%). Data: LCMS (B) $R_t$: 8.105 min; m/z 368.1 (M+H)$^+$.

Example 76

4-(6-Fluoro-1H-indol-3-yl)-N-[(4-fluoro-4-piperidyl)methyl]benzamide

This compound was prepared from Intermediate 3 and tert-butyl 4-(aminomethyl)-4-fluoropiperidine-1-carboxylate hydrochloride according to the procedure described in Example 1. Purification was performed, after Boc-deprotection, using preparative HPLC to afford the title compound (15 mg, 25%). Data: LCMS (B) $R_t$: 7.633 min; m/z 370.1 (M+H)$^+$.

Example 77

4-(6-Fluoro-1H-indol-3-yl)-N-(2-pyrrolidin-1-yl-ethyl)benzamide

This compound was prepared from Intermediate 3 and 1-(2-aminoethyl)pyrrolidine according to the procedure described in Example 1. Purification was performed using preparative HPLC to afford the title compound (29.3 mg, 76%). Data: LCMS (B) $R_t$: 7.620 min; M/z 352.2 (M+H)$^+$.

Example 78

N-[3-(dimethylamino)-2-hydroxy-propyl]-4-(6-fluoro-1H-indol-3-yl)benzamide

This compound was prepared from Intermediate 3 and 1-amino-3-(dimethylamino)propan-2-ol according to the procedure described in Example 1. Purification was performed using preparative HPLC to afford the title compound (11.5 mg, 29%). Data: LCMS (B) $R_t$: 7.111 min; m/z 356.1 (M+H)$^+$.

Example 79

N-[2-(diethylamino)-1-methyl-ethyl]-4-(6-fluoro-1H-indol-3-yl)-2-methoxy-benzamide This compound was prepared from Intermediate 8 and N1,N1-diethylpropane-1,2-diamine according to the procedure described in Example 1. Purification was performed using preparative HPLC to afford the title compound (22.4 mg, 51%). Data: LCMS (B) $R_t$: 8.536 min; m/z 398.2 (M+H)$^+$.

Example 80

N-[4-(6-fluoro-1H-indol-3-yl)phenyl]-2-methylsulfonyl-acetamide

This compound was prepared from Intermediate 5 and methanesulfonylacetic acid according to the procedure described in Example 1. Purification was performed using preparative HPLC to afford the title compound (15.4 mg, 40.4%). Data: LCMS (B) $R_t$: 10.373 min; m/z 347.0 $(M+H)^+$.

Example 81

N-(2-diethylaminoethyl)-4-(6-fluoro-1H-indol-3-yl)benzamide

This compound was prepared from Intermediate 3 and N,N-diethylethylenediamine according to the procedure described in Example 1. Purification was performed using preparative HPLC to afford the title compound (15.4 mg, 40.4%). Data: LCMS (B) $R_t$: 10.373 min; m/z 347.0 $(M+H)^+$.

Example 82

2-Chloro-N-[2-(dimethylamino)-1-methyl-ethyl]-4-(6-fluoro-1H-indol-3-yl)benzamide This compound was prepared from Intermediate 8 and N1,N1-dimethylpropane-1,2-diamine according to the procedure described in Example 1. Purification was performed using preparative HPLC to afford the title compound (10.3 mg, 32%). Data: LCMS (B) $R_t$: 8.108 min; m/z 374.1 $(M+H)^+$ (chloride pattern).

Example 83

N-(azepan-4-yl)-4-(6-fluoro-1H-indol-3-yl)benzamide

This compound was prepared from Intermediate 3 and 1-N-Boc-hexahydro-1H-azepin-4-amine according to the procedure described in Example 1. Purification was performed, after Boc-deprotection, using preparative HPLC to afford the title compound (13 mg, 33%). Data: LCMS (B) $R_t$: 7.495 min; m/z 352.2 $(M+H)^+$.

Example 84

4-(6-Fluoro-1H-indol-3-yl)-N-[[(2S)-pyrrolidin-2-yl]methyl]benzamide

This compound was prepared from Intermediate 3 and (S)-2-(aminomethyl)-1-N-Boc-pyrrolidine according to the procedure described in Example 1. Purification was performed, after Boc-deprotection, using preparative HPLC to afford the title compound (12.5 mg, 23%). Data: LCMS (B) $R_t$: 7.535 min; m/z 338.1 $(M+H)^+$.

Example 85

(3-Aminopyrazol-1-yl)-[4-(6-fluoro-1H-indol-3-yl)phenyl]methanone

This compound was prepared from Intermediate 3 and 3-aminopyrazole according to the procedure described in Example 1. Purification was performed using preparative HPLC to afford the title compound (5 mg, 15%). Data: LCMS (B) $R_t$: 11.261 min; m/z 321.1 $(M+H)^+$.

Example 86

N-cyclopropyl-4-(6-fluoro-1H-indol-3-yl)benzamide

This compound was prepared from Intermediate 3 and cyclopropylamine according to the procedure described in Example 1. Purification was performed using preparative HPLC to afford the title compound (17 mg, 52%). Data: LCMS (B) $R_t$: 11.017 min; m/z 395.1 $(M+H)^+$.

Example 87

4-(6-Fluoro-1H-indol-3-yl)-N-[(1S,2S)-2-hydroxycyclopentyl]benzamide

This compound was prepared from Intermediate 3 and trans-(1S,2S)-2-aminocyclopentanol hydrochloride according to the procedure described in Example 1. Purification was performed using preparative HPLC to afford the title compound (16 mg, 43%). Data: LCMS (B) $R_t$: 10.628 min; m/z 339.1 $(M+H)^+$.

Example 88

4-(6-Fluoro-1H-indol-3-yl)-N-[(1S)-1,2,2-trimethylpropyl]benzamide

This compound was prepared from Intermediate 3 and (S)-(+)-3,3-Dimethyl-2-butylamine according to the procedure described in Example 1. Purification was performed using preparative HPLC to afford the title compound (37 mg, 99%). Data: LCMS (B) $R_t$: 14.798 min; m/z 339.2 $(M+H)^+$.

Example 89

4-(6-Fluoro-1H-indol-3-yl)-N-[(1-hydroxycyclohexyl)methyl]benzamide

This compound was prepared from Intermediate 3 and 1-aminomethyl-1-cyclohexanol hydrochloride according to the procedure described in Example 1. Purification was performed using preparative HPLC to afford the title compound (38 mg, 94%). Data: LCMS (B) $R_t$: 12.278 min; m/z 367.1 $(M+H)^+$.

Example 90

N-(2-aminoethyl)-4-(6-fluoro-1H-indol-3-yl)benzamide

This compound was prepared from Intermediate 3 and tert-butyl N-(2-aminoethyl) carbamate according to the procedure described in Example 1. Purification was performed, after Boc-deprotection, using preparative HPLC to afford the title compound (7 mg, 58%). Data: LCMS (B) $R_t$: 6.840 min; m/z 298.1 $(M+H)^+$.

Example 91

4-(6-Fluoro-1H-indol-3-yl)-N-[[(3S)-pyrrolidin-3-yl]methyl]benzamide

This compound was prepared from Intermediate 3 and (R)-3-(aminomethyl)-1-N-Boc-pyrrolidine according to the procedure described in Example 1. Purification was performed, after Boc-deprotection, using preparative HPLC to

Example 92

4-(6-Fluoro-1H-indol-3-yl)-N-[[(3S)-1-(isopropyl-carbamothioyl)-3-piperidyl]methyl]benzamide This compound was prepared from Intermediate 3 and (S)-1-Boc-3-(aminomethyl)piperidine according to the procedure described in Example 1. Purification was performed, after Boc-deprotection and subsequent reaction with isopropyl isothiocyanate, using preparative HPLC to afford the title compound. Data: LCMS (B) $R_t$: 13.346 min; m/z 453.2 (M+H)$^+$.

Example 93

4-(6-Fluoro-1H-indol-3-yl)-N-morpholino-benzamide

This compound was prepared from Intermediate 3 and N-aminomorpholine according to the procedure described in Example 1. Purification was performed using preparative HPLC to afford the title compound (8.2 mg, 22%). Data: LCMS (B) $R_t$: 9.267 min; m/z 340.1 (M+H)$^+$.

Example 94

4-(6-Fluoro-1H-indol-3-yl)-N-[[(3S)-3-piperidyl]methyl]benzamide

This compound was prepared from Intermediate 3 and (R)-1-Boc-3-(aminomethyl)piperidine according to the procedure described in Example 1. Purification was performed, after Boc-deprotection, using preparative HPLC to afford the title compound (14 mg, 36%). Data: LCMS (B) $R_t$: 7.615 min; m/z 352.1 (M+H)$^+$.

Example 95

4-(6-Fluoro-1H-indol-3-yl)-N-[[(3R)-pyrrolidin-3-yl]methyl]benzamide

This compound was prepared from Intermediate 3 and (S)-3-(aminomethyl)-1-N-Boc-pyrrolidine according to the procedure described in Example 1. Purification was performed, after Boc-deprotection, using preparative HPLC to afford the title compound (3 mg, 8%). Data: LCMS (B) $R_t$: 7.251 min; m/z 338.1 (M+H)$^+$.

Example 96

N-[4-(6-fluoro-1H-indol-3-yl)phenyl]-3-phenyl-propanamide

This compound was prepared from Intermediate 5 and 3-phenylpropionic acid according to the procedure described in Example 1. Purification was performed using preparative HPLC to afford the title compound (18.0 mg, 45.7%). Data: LCMS (B) $R_t$: 14.591 min; m/z 359.1 (M+H)$^+$.

Example 97

N-[4-(6-Fluoro-1H-indol-3-yl)phenyl]-6-azaspiro[2.5]octane-2-carboxamide

This compound was prepared from Intermediate 5 and 6-(tert-butoxycarbonyl)-6-azaspiro[2.5]octane-1-carboxylic acid according to the procedure described in Example 1. Purification was performed, after Boc-deprotection, using preparative HPLC to afford the title compound (16.2 mg, 40.4%). Data: LCMS (B) $R_t$: 8.186 min; m/z 364.1 (M+H)$^+$.

Example 98

N-[4-(6-fluoro-1H-indol-3-yl)phenyl]-2-(1-hydroxy-cyclopentyl)acetamide

This compound was prepared from Intermediate 5 and 2-(1-hydroxycyclopentyl)acetic acid according to the procedure described in Example 1. Purification was performed using preparative HPLC to afford the title compound (6.3 mg, 16.1%). Data: LCMS (B) $R_t$: 12.463 min; m/z 353.1 (M+H)$^+$.

Example 99

N-[4-(6-Fluoro-/H-indol-3-yl)phenyl]-2-(5-methyl-isoxazol-3-yl)acetamide

This compound was prepared from Intermediate 5 and 2-(5-methylisoxazol-3-yl)acetic acid according to the procedure described in Example 1. Purification was performed using preparative HPLC to afford the title compound (11.7 mg, 30.3%). Data: LCMS (B) $R_t$: 12.092 min; m/z 350.1 (M+H)$^+$.

Example 100

(1R,5S)—N-[4-(6-fluoro-1H-indol-3-yl)phenyl]-3-oxabicyclo[3.1.0]hexane-6-carboxamide This compound was prepared from Intermediate 5 and (1R,5S)-3-oxabicyclo-[3.1.0]hexane-6-carboxylic acid according to the procedure described in Example 1. Purification was performed using preparative HPLC to afford the title compound (26.6 mg, 71.8%). Data: LCMS (B) $R_t$: 11.456 min; m/z 337.1 (M+H)$^+$.

Example 101

2,2-Difluoro-N-[4-(6-fluoro-1H-indol-3-yl)phenyl]cyclobutanecarboxamide

This compound was prepared from Intermediate 5 and 2,2-difluorocyclobutanecarboxylic acid according to the procedure described in Example 1. Purification was performed using preparative HPLC to afford the title compound (14.9 mg, 39.3%). Data: LCMS (B) $R_t$: 13.239 min; m/z 345.1 (M+H)$^+$.

Example 102

N-[4-(6-fluoro-1H-indol-3-yl)phenyl]-2-morpholin-2-yl-acetamide

This compound was prepared from Intermediate 5 and 2-(4-tert-butoxycarbonylmorpholin-2-yl)acetic acid according to the procedure described in Example 1. Purification was performed, after Boc-deprotection, using preparative (Example 91 continued top of column:) afford the title compound (8 mg, 21%). Data: LCMS (B) $R_t$: 7.225 min; m/z 338.1 (M+H)$^+$.

Example 103

(1R,3S)-3-amino-N-[4-(6-fluoro-1H-indol-3-yl)phenyl]cyclohexanecarboxamide

This compound was prepared from Intermediate 5 and (1R,3S)-3-(tert-butoxycarbonylamino)cyclohexanecarboxylic acid according to the procedure described in Example 1. Purification was performed, after Boc-deprotection, using preparative HPLC to afford the title compound (4.7 mg, 12.3%). Data: LCMS (B) $R_t$: 8.258 min; m/z 352.2 (M+H)$^+$.

Example 104

N-[4-(6-fluoro-1H-indol-3-yl)phenyl]-3-azabicyclo[3.1.0]hexane-6-carboxamide

This compound was prepared from Intermediate 5 and 3-tert-butoxycarbonyl-3-azabicyclo[3.1.0]hexane-6-carboxylic acid according to the procedure described in Example 1. Purification was performed, after Boc-deprotection, using preparative HPLC to afford the title compound (7.9 mg, 21.4%). Data: LCMS (B) $R_t$: 7.676 min; m/z 336.1 (M+H)$^+$.

Example 105

(1S,3R)-3-amino-N-[4-(6-fluoro-1H-indol-3-yl)phenyl]cyclohexanecarboxamide

This compound was prepared from Intermediate 5 and (1S,3R)-3-(tert-butoxycarbonylamino)cyclohexanecarboxylic acid according to the procedure described in Example 1. Purification was performed, after Boc-deprotection, using preparative HPLC to afford the title compound (2 mg, 5.1%). Data: LCMS (B) $R_t$: 8.285 min; m/z 352.1 (M+H)$^+$.

Example 106

(1R,3S)-3-amino-N-[4-(6-fluoro-1H-indol-3-yl)phenyl]cyclopentanecarboxamide

This compound was prepared from Intermediate 5 and (1R,3S)-3-(tert-butoxycarbonylamino)cyclopentanecarboxylic acid according to the procedure described in Example 1. Purification was performed, after Boc-deprotection, using preparative HPLC to afford the title compound (7.7 mg, 20.8%). Data: LCMS (B) $R_t$: 7.834 min; m/z 338.1 (M+H)$^+$.

Example 107

N-[4-(6-fluoro-1H-indol-3-yl)phenyl]-3-(1-methylpyrazol-4-yl)propanamide

This compound was prepared from Intermediate 5 and 3-(1-methylpyrazol-4-yl)propanoic acid according to the procedure described in Example 1. Purification was performed using preparative HPLC to afford the title compound (27.2 mg, 68.2%). Data: LCMS (B) $R_t$: 10.958 min; m/z 363.1 (M+H)$^+$.

Example 108

N-[4-(6-fluoro-1H-indol-3-yl)phenyl]-1-methyl-6-oxo-piperidine-3-carboxamide

This compound was prepared from Intermediate 5 and 1-methyl-6-oxo-piperidine-3-carboxylic acid according to the procedure described in Example 1. Purification was performed using preparative HPLC to afford the title compound (11.7 mg, 29.2%). Data: LCMS (B) $R_t$: 10.175 min; m/z 366.1 (M+H)$^+$.

Example 109

N-[4-(6-fluoro-1H-indol-3-yl)phenyl]-2-(4-methyl-piperazin-1-yl)acetamide

This compound was prepared from Intermediate 5 and (4-methyl-piperazin-1-yl)-acetic acid according to the procedure described in Example 1. Purification was performed using preparative HPLC to afford the title compound (15.3 mg, 37.8%). Data: LCMS (B) $R_t$: 7.412 min; m/z 367.1 (M+H)$^+$.

Example 110

(3R,4R)—N-[4-(6-fluoro-1H-indol-3-yl)phenyl]-3-methyl-piperidine-4-carboxamide

This compound was prepared from Intermediate 5 and cis-1-N-Boc-3-methyl-piperidine-4-carboxylic acid according to the procedure described in Example 1. Purification was performed, after Boc-deprotection, using preparative HPLC to afford the title compound (10.7 mg, 27.6%). Data: LCMS (B) $R_t$: 8.058 min; m/z 352.2 (M+H)$^+$.

Example 111

4-(6-Fluoro-1H-indol-3-yl)-N-[(1R)-2-hydroxy-1-methyl-ethyl]-2-methoxy-benzamide This compound was prepared from Intermediate 8 and (2R)-2-aminopropan-1-ol according to the procedure described in Example 1. Purification was performed using preparative HPLC to afford the title compound (6.7 mg, 18%). Data: LCMS (B) $R_t$: 10.385 min; M/z 343.1 (M+H)$^+$.

Example 112

N-(2-amino-2-oxo-ethyl)-4-(6-fluoro-1H-indol-3-yl)benzamide

This compound was prepared from Intermediate 3 and glycinamide hydrochloride according to the procedure described in Example 1. Purification was performed using preparative HPLC to afford the title compound (3.7 mg, 11%). Data: LCMS (B) $R_t$: 8.436 min; m/z 312.1 (M+H)$^+$.

Example 113

N-(2-acetamidoethyl)-4-(6-fluoro-1H-indol-3-yl)benzamide

This compound was prepared from Intermediate 3 and N-acetylethylenediamine according to the procedure described in Example 1. Purification was performed using preparative HPLC to afford the title compound (15.6 mg, 42%). Data: LCMS (B) $R_t$: 8.996 min; m/z 340.1 (M+H)$^+$.

Example 114

N-(3,3-difluorocyclobutyl)-4-(6-fluoro-1H-indol-3-yl)benzamide

This compound was prepared from Intermediate 3 and 3,3-difluorocyclobutanamine hydrochloride according to the (continues: HPLC to afford the title compound (8.7 mg, 22.4%). Data: LCMS (B) $R_t$: 7.625 min; m/z 354.1 (M+H)$^+$.)

Example 115

2-Chloro-N-[2-[(3S,4S)-3,4-dihydroxypyrrolidin-1-yl]ethyl]-4-(6-fluoro-1H-indol-3-yl)benzamide This compound was prepared from Intermediate 6 and (3S,4S)-1-(2-aminoethyl)pyrrolidine-3,4-diol dihydrochloride according to the procedure described in Example 1. Purification was performed using preparative HPLC to afford the title compound (6 mg, 17%). Data: LCMS (B) $R_t$: 7.504 min; m/z 418.1 (M+H)$^+$.

Example 116

2-Chloro-N-[2-[(3R,4R)-3,4-dihydroxypyrrolidin-1-yl]ethyl]-4-(6-fluoro-1H-indol-3-yl)benzamide This compound was prepared from Intermediate 6 and (3R,4R)-1-(2-aminoethyl)pyrrolidine-3,4-diol dihydrochloride according to the procedure described in Example 1. Purification was performed using preparative HPLC to afford the title compound (6.7 mg, 19%). Data: LCMS (B) $R_t$: 7.511 min; m/z 418.1 (M+H)$^+$.

Example 117

3-Fluoro-4-(6-fluoro-1H-indol-3-yl)-N-[(1R)-2-hydroxy-1-methyl-ethyl]benzamide (a) 3-Fluoro-N-[(1R)-2-hydroxy-1-methyl-ethyl]-4-(4,4,5,5-tetramethyl-1,3,2-dioxaborolan-2-yl)benzamide To a stirred solution of 3-fluoro-4-(4,4,5,5-tetramethyl-1,3,2-dioxaborolan-2-yl)benzoic acid (109 mg, 0.59 mmol) and (2R)-2-aminopropan-1-ol (42 µl, 0.71 mmol) in DMF (5 ml) was added subsequently, HOBt (96 mg, 0.71 mmol) triethylamine (247 µl, 1.77 mmol) and EDCl hydrochloride (136 mg, 0.71 mmol). The reaction mixture was stirred at room temperature o/w. The mixture was poured into water/brine/ethyl acetate=1/1/1 v/v % (100 ml) and stirred for 10 min. The organic layer was separated, washed with brine, dried over sodium sulfate, filtered and concentrated in vacuo to give 44 mg of the title compound.

(b) 3-Fluoro-4-[6-fluoro-1-(p-tolylsulfonyl)indol-3-yl]-N-[(1R)-2-hydroxy-1-methyl-ethyl]benzamide 3-Bromo-6-fluoro-1-(p-tolylsulfonyl)indole (30 mg, 0.08 mmol) and 3-fluoro-N-[(1R)-2-hydroxy-1-methyl-ethyl]-4-(4,4,5,5-tetramethyl-1,3,2-dioxaborolan-2-yl)benzamide (44 mg, 0.136 mmol) were dissolved in dioxane (1 ml) and solution of 2N $K_2CO_3$ in water (0.2 ml, 0.41 mmol) was added. The mixture was purged with nitrogen for 5 min after which PdCl$_2$(dppf) (13 mg, 0.016 mmol) was added. The mixture was stirred under $N_2$-atmosphere for another 3 min. The reaction mixture was heated for 6 hours at 120° C. under microwave radiation. The mixture was diluted with dichloromethane and filtered over Decalite™. The filtrate was evaporated and the crude product was purified by column chromatography (dichloromethane to methanol=10/0 to 9/1 v/v %) to afford 16 mg of 3-fluoro-4-[6-fluoro-1-(p-tolylsulfonyl)indol-3-yl]-N-[(1R)-2-hydroxy-1-methyl-ethyl]benzamide (41% yield).

(c) 3-Fluoro-4-(6-fluoro-1H-indol-3-yl)-N-[(1R)-2-hydroxy-1-methyl-ethyl]benzamide Deprotection of 3-fluoro-4-[6-fluoro-1-(p-tolylsulfonyl)indol-3-yl]-N-[(1R)-2-hydroxy-1-methyl-ethyl]benzamide was performed according to the procedure described in Example 3. Purification was performed using preparative HPLC to afford the title compound (1.1 mg, 10%). Data: LCMS (B) $R_t$: 10.033 min; m/z 331.1 (M+H)$^+$.

Example 118

4-(6-Fluoro-1H-indol-3-yl)-N-(3-piperidyl)benzamide

This compound was prepared from Intermediate 3 and (+/−)-3-amino-1-N-Boc-piperidine according to the procedure described in Example 1. Purification was performed, after Boc-deprotection, using preparative HPLC to afford the title compound (234 mg, 72%). Data: LCMS (B) $R_t$: 7.374 min; m/z 338.1 (M+H)$^+$.

Example 119

N-(1-acetyl-3-piperidyl)-4-(6-fluoro-1H-indol-3-yl)benzamide

To a cold (4° C.) solution of 4-(6-Fluoro-1H-indol-3-yl)-N-(3-piperidyl)benzamide (Example 118, 25 mg, 0.07 mmol) and DIPEA (26.2 µL, 0.15 mmol) in DCM (1 mL) and DMA (0.3 mL) was added drop-wise a solution of acetyl chloride (5.4 µl, 0.07 mmol) in DCM (0.5 mL). The reaction mixture was allowed to warm-up to room temperature and stirred for 2 h. The reaction was quenched by addition of aq. sat. NH$_4$Cl-solution and ethyl acetate was added. The organic layer was separated, washed with brine, dried over sodium sulfate, filtered and concentrated in vacuo. The crude product was triturated with acetonitrile. The white solids were filtered, washed with diethyl ether and dried to give 13 mg of the title compound (yield: 49%). Data: LCMS (B) $R_t$: 10.240 min; m/z 380.2 (M+H)$^+$.

Example 120

4-(6-Fluoro-1H-indol-3-yl)-N-(1-methylsulfonyl-3-piperidyl)benzamide

This compound was prepared from Example 118 and methanesulfonyl chloride according to the procedure described in Example 119 to afford the title compound (12 mg, 41%). Data: LCMS (B) $R_t$: 11.197 min; m/z 416.1 (M+H)$^+$.

Example 121

Ethyl 3-[[4-(6-fluoro-1H-indol-3-yl)benzoyl]amino]piperidine-1-carboxylate

This compound was prepared from Example 118 and ethyl chloroformate according to the procedure described in Example 119 to afford the title compound (14 mg, 48%). Data: LCMS (B) $R_t$: 12.616 min; m/z 410.2 (M+H)$^+$.

Example 122

Methyl 2-[[4-(6-fluoro-1H-indol-3-yl)benzoyl]amino]-2-(4-piperidyl)acetate

This compound was prepared from Intermediate 3 and 4-(amino-methoxycarbonyl-methyl)-piperidine-1-carboxylic acid tert-butyl ester according to the procedure described in Example 1. Purification was performed, after Boc-deprotection, using preparative HPLC to afford the title compound (22 mg, 76%). Data: LCMS (B) $R_t$: 7.969 min; m/z 410.2 (M+H)$^+$.

Example 123

2-Fluoro-4-(6-fluoro-1H-indol-3-yl)-N-[(1S)-2-hydroxy-1-methyl-ethyl]benzamide

This compound was prepared from Intermediate 9 and (2S)-2-aminopropan-1-ol according to the procedure described in Example 1. Purification was performed using preparative HPLC to afford the title compound (7.2 mg, 30%). Data: LCMS (B) $R_t$: 10.135 min; m/z 331.1 (M+H)$^+$.

Example 124

N-[3-(dimethylamino)propyl]-2-fluoro-4-(6-fluoro-1H-indol-3-yl)benzamide

This compound was prepared from Intermediate 9 and N,N-dimethylpropane-1,3-diamine according to the procedure described in Example 1. Purification was performed using preparative HPLC to afford the title compound (8 mg, 34%). Data: LCMS (B) $R_t$: 7.487 min; m/z 358.1 (M+H)$^+$.

Example 125

2-Fluoro-4-(6-fluoro-1H-indol-3-yl)-N-[(3S)-3-piperidyl]benzamide

This compound was prepared from Intermediate 9 and tert-butyl (3S)-3-amino-piperidine-1-carboxylate according to the procedure described in Example 1. Purification was performed, after Boc-deprotection using preparative HPLC to afford the title compound (9.6 mg, 30%). Data: LCMS (B) $R_t$: 7.655 min; m/z 356.1 (M+H)$^+$.

Example 126

4-(6-Fluoro-1H-indol-3-yl)-N-[(1S)-2-hydroxy-1-methyl-ethyl]-3-methyl-benzamide

This compound was prepared from Intermediate 10 and (2S)-2-aminopropan-1-ol according to the procedure described in Example 1. Purification was performed using preparative HPLC to afford the title compound (8.5 mg, 31%). Data: LCMS (B) $R_t$: 10.161 min; m/z 327.1 (M+H)$^+$.

Example 127

N-[3-(dimethylamino)propyl]-4-(6-fluoro-1H-indol-3-yl)-3-methyl-benzamide

This compound was prepared from Intermediate 10 and N,N-dimethylpropane-1,3-diamine according to the procedure described in Example 1. Purification was performed using preparative HPLC to afford the title compound (8.7 mg, 35%). Data: LCMS (B) $R_t$: 7.766 min; m/z 354.2 (M+H)$^+$.

Example 128

4-(6-Fluoro-1H-indol-3-yl)-N-[(1R)-2-hydroxy-1-methyl-ethyl]-3-methyl-benzamide

This compound was prepared from Intermediate 10 and (2S)-2-aminopropan-1-ol according to the procedure described in Example 1. Purification was performed using preparative HPLC to afford the title compound (11.5 mg, 68%). Data: LCMS (B) $R_t$: 10.160 min; m/z 327.1 (M+H)$^+$.

Example 129

2-Fluoro-4-(6-fluoro-1H-indol-3-yl)-N-[(1R)-2-hydroxy-1-methyl-ethyl]benzamide

This compound was prepared from Intermediate 9 and (2S)-2-aminopropan-1-ol according to the procedure described in Example 1. Purification was performed using preparative HPLC to afford the title compound (0.7 mg, 6%).

Example 130

4-(6-Fluoro-1H-indol-3-yl)-3-methyl-N-[(3S)-3-piperidyl]benzamide

This compound was prepared from Intermediate 10 and tert-butyl (3S)-3-amino-piperidine-1-carboxylate according to the procedure described in Example 1. Purification was performed, after Boc-deprotection, using preparative HPLC to afford the title compound (30 mg, 66%). Data: LCMS (B) $R_t$: 7.981 min; m/z 352.2 (M+H)$^+$.

Example 131

(3R)—N-[4-(6-fluoro-1H-indol-3-yl)phenyl]piperidine-3-carboxamide

This compound was prepared from Intermediate 5 and (R)-piperidine-1,3-dicarboxylic acid 1-benzyl ester according to the procedure described in Example 1. Purification was performed, after Cbz-deprotection (10% Pd/C, catalytic hydrogenation), using preparative HPLC to afford the title compound (8.8 mg, 20%). Data: LCMS (B) $R_t$: 7.814 min; m/z 338.1 (M+H)$^+$.

Example 132

4-(6-Fluoro-1H-indol-3-yl)-N-(1-sulfamoyl-3-piperidyl)benzamide

To a cold (0° C.) solution of chlorosulfonyl isocyanate (12.3 μl, 0.14 mmol) in dichloromethane (1 ml) was added dropwise a solution of t-BuOH (14.3 μl, 0.15 mmol) in dichloromethane (1 ml) maintaining the temperature around 0° C. The mixture was stirred for 45 min at 0° C. To the reaction mixture was added a suspension of 4-(6-fluoro-1H-indol-3-yl)-N-(3-piperidyl)benzamide (Example 118, 47.1 mg, 0.14 mmol) and triethylamine (38.9 μl, 0.28 mmol). The reaction mixture was allowed to warm-up to room temperature in 1 h and was stirred for an additional 2 h at room temperature. The reaction was quenched by addition of aq.

sat. NH₄Cl-solution and ethyl acetate was added. The organic layer was separated, washed with brine, dried over sodium sulfate, filtered and concentrated in vacuo. The crude product was triturated with methanol. The white solids were filtered, washed with diethyl ether and dried to give 28 mg of tert-butyl N-[[3-[[4-(6-fluoro-1H-indol-3-yl)benzoyl]amino]-1-piperidyl]sulfonyl]carbamate (yield: 38%). Purification was performed, after Boc-deprotection, using preparative HPLC to afford the title compound (4 mg, 24%). Data: LCMS (B) $R_t$: 10.424 min; m/z 417.1 (M+H)⁺.

Example 133

4-(6-Fluoro-1H-indol-3-yl)-N-[(3R)-quinuclidin-3-yl]benzamide

This compound was prepared from Intermediate 3 and (R)-(+)-3-aminoquinuclidine dihydrochloride according to the procedure described in Example 1. Purification was performed using preparative HPLC to afford the title compound (15 mg, 37%). Data: LCMS (B) $R_t$: 7.573 min; m/z 364.2 (M+H)⁺.

Example 134

4-(6-Fluoro-1H-indol-3-yl)-N-(3,3,3-trifluoropropyl)benzamide

This compound was prepared from Intermediate 3-a and 3,3,3-trifluoropropan-1-amine according to the procedure described in Example 3. Purification was performed using preparative HPLC to afford the title compound (16 mg, 54%). Data: LCMS (B) $R_t$: 12.622 min; m/z 351.1 (M+H)⁺.

Example 135

4-(6-Fluoro-1H-indol-3-yl)-N-[3-(4-methylpiperazin-1-yl)propyl]benzamide

This compound was prepared from Intermediate 3 and 1-(3-aminopropyl)-4-methylpiperazine according to the procedure described in Example 1. Purification was performed using preparative HPLC to afford the title compound (16.8 mg, 35%). Data: LCMS (B) $R_t$: 6.323 min; m/z 395.2 (M+H)⁺.

Example 136

4-(6-Fluoro-1H-indol-3-yl)-N-[(1S)-2-hydroxy-1-methyl-ethyl]-2-methoxy-benzamide This compound was prepared from Intermediate 8 and (2S)-2-aminopropan-1-ol according to the procedure described in Example 1. Purification was performed using preparative HPLC to afford the title compound (11.4 mg, 30%). Data: LCMS (B) $R_t$: 10.402 min; m/z 343.1 (M+H)⁺.

Example 137

N-[3-(dimethylamino)propyl]-4-(6-fluoro-1H-indol-3-yl)-2-methoxy-benzamide

This compound was prepared from Intermediate 8 and N,N-dimethylpropane-1,3-diamine according to the procedure described in Example 1. Purification was performed using preparative HPLC to afford the title compound (18.8 mg, 46%). Data: LCMS (B) $R_t$: 7.833 min; m/z 370.2 (M+H)⁺.

Example 138

Methyl 2-[[4-(6-fluoro-1H-indol-3-yl)benzoyl]amino]acetate

This compound was prepared from Intermediate 3-a and methyl 2-aminoacetate hydrochloride according to the procedure described in Example 3. Purification was performed using preparative HPLC to afford the title compound (6.7 mg, 23%). Data: LCMS (B) $R_t$: 10.092 min; m/z 327.1 (M+H)⁺.

Example 139

Biochemical Assay for TDO

The NFK GreenScreen™ assay technology was also used to determine the inhibitory activity of compounds on TDO (Seegers, N., et al., J. Biol. Screen. 19: 1266; 2014). Compounds were serially diluted in DMSO and finally in TDO reaction buffer, consisting of 100 mM NaH₂PO₄, pH 7.0, supplemented with 0.02% Tween-20 (cat. No. P7949; Sigma Aldrich). Recombinant TDO (Seegers, N., et al.) and all other assay components were diluted in TDO reaction buffer. 10 µl of compound solution and 20 µl of enzyme solution supplemented with 200 µM ascorbic acid were combined in the well of a black 384-well plate (cat. no. 3573; Corning, Corning, N.Y., USA), and incubated for 60 min at room temperature. Subsequently, 10 µl of 0.8 mM of the substrate L-tryptophan was added, i.e., the final concentration of L-tryptophan was 200 µM. The DMSO concentration in the assay was 0.3%. The concentration of TDO was 50 nM. Incubation was continued for 15 min at room temperature. Then, 10 µl of NFK Green™ (NTRC, Oss, The Netherlands) was added, the plate was sealed, and the reaction was developed for 3 hours at 37° C. To determine the production of N-formyl kynurenine (NFK), the seal was removed and fluorescence was read on an EnVision multimode reader (Perkin Elmer, Waltham, Mass., USA). $IC_{50}$ were calculated using XLfit™ software (ID Business Solutions, Ltd., Surrey, U.K.). The $IC_{50}$ values of all exemplified compounds were found to be smaller than 25 µM. Compounds of examples 6, 7, 16, 28, 45, 80, 85, 88, 89, 92, 96, 99, 100, 108, 111, 113, 119, 126, 128, 132, 134 showed an $IC_{50}$ value >1 µM and <5 µM and compounds of examples 1, 2, 3, 4, 5, 8, 9, 10, 12, 13, 14, 15, 17, 18, 19, 20, 21, 22, 23, 24, 25, 26, 27, 29, 30, 31, 32, 33, 34, 35, 36, 37, 38, 39, 40, 41, 42, 43, 44, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 81, 82, 83, 84, 86, 87, 90, 91, 93, 94, 95, 97, 98, 102, 103, 104, 105, 106, 109, 110, 112, 115, 116, 117, 118, 121, 122, 123, 124, 125, 127, 129, 130, 131, 133, 135, 136, 137, 138 showed an $IC_{50}$ of <1 µM.

Example 140

Cell-Based Assay for TDO

The NFK GreenScreen™ assay technology was also used to determine the inhibitory activity of compounds on TDO in SW48 colorectal carcinoma cells (Seegers, N., et al., J. Biol. Screen. 19: 1266; 2014). SW48 colorectal carcinoma cells were purchased from LGC Standards GmbH (Wesel, Germany) and cultured in RPMI 1640 tissue culture medium (Life Technologies, Bleiswijk, The Netherlands), supplemented with 10% (v/v) bovine calf serum. Compounds were dissolved in DMSO and diluted in RPMI 1640. Final DMSO concentration in the assay was 0.4% (v/v). Eight thousand cells per well in 40 µl were seeded in a black 384-well tissue plate (cat. No. 781086; Greiner Bio-One GmbH, Frickenhausen, Germany) and allowed to adhere by incubation at 37° C., 95% humidity, and 5% $CO_2$ for 3 h. Then, 5 µl of compound solution was added to the cells. After incubation for 1 hour, 5 µl of L-tryptophan in RPMI 1640 was added and incubation was continued for 18 hours. To determine NFK levels, 12 µl NFK Green™ (NTRC, Oss, The Netherlands) was added to each well, and the plate was sealed and incubated for 4 hours at 37° C. Fluorescence was measured on an EnVision multimode reader (Perkin Elmer, Waltham, Mass., USA). $IC_{50}$ were calculated using XLfit™ software (ID Business Solutions, Ltd., Surrey, U.K.). The $IC_{50}$ values of all exemplified compounds were found to be smaller than 2 µM. Compounds of examples 3, 4, 10, 12, 13, 14, 16, 17, 26, 27, 31, 36, 42, 43, 44, 45, 46, 47, 48, 49, 50, 51, 53, 56, 57, 59, 60, 61, 62, 63, 64, 66, 86, 87, 93, 94, 95, 97, 100, 102, 103, 104, 105, 106, 107, 109, 110, 111, 112, 113, 114, 115, 116, 117, 119, 120, 122, 127, 129, 131, 132, 136 showed an $IC_{50}$ value >200 nM and <500 nM and compounds of examples 1, 2, 8, 15, 19, 20, 21, 23, 24, 25, 52, 54, 55, 58, 68, 69, 70, 71, 72, 73, 74, 75, 76, 77, 78, 79, 80, 81, 82, 83, 84, 118, 123, 124, 125, 133, 134, 135, 137 showed an $IC_{50}$ of <200 nM.

Example 141

Biochemical IDO1 Assay

To determine the inhibitory activity of compounds on IDO1, the NFK GreenScreen™ assay technology was used, which makes use of a chemical probe to detect NFK (Seegers, N., et al., J. Biol. Screen. 19: 1266; 2014). Compounds were serially diluted in dimethylsulfoxide (DMSO) and finally in IDO1 reaction buffer, consisting of 50 mM $NaH_2PO_4$, pH 7.0, supplemented with 0.1% Tween-20 (cat. No. P7949; Sigma Aldrich) and 2% glycerol. Recombinant full-length IDO1 (Seegers, N., et al.) and all other assay components were diluted in IDO1 reaction buffer. 10 µl of compound solution, 20 µl of enzyme solution supplemented with 20 mM ascorbic acid, 20 µg/ml catalase, and 20 µM methylene blue were combined in the well of a black 384-well plate (cat. no. 3573; Corning, Corning, N.Y., USA) and incubated for 30 min at room temperature. Subsequently, 10 µl of 0.4 mM of the substrate L-tryptophan was added, i.e., the final concentration of L-tryptophan was 100 µM. The DMSO concentration in the assay was 0.3%. The concentration of IDO1 was 25 nM. Incubation was continued for 60 min at room temperature. Then, 10 µl of NFK Green™ (NTRC, Oss, The Netherlands) was added, the plate was sealed, and the reaction was developed for 3 hours at 37° C. To determine the production of N-formyl kynurenine (NFK), the seal was removed and fluorescence was read on an EnVision multimode reader (Perkin Elmer, Waltham, Mass., USA). $IC_{50}$ were calculated using XLfit™ software (ID Business Solutions, Ltd., Surrey, U.K.). The $IC_{50}$ values of all exemplified compounds were found to be higher than 25 µM.

Example 143

Cytochrome P450 Assays

To determine the inhibitory potency of compounds on CYP3A4 enzyme, the P450-Glo CYP3A4 luciferin isopropylacetal (Luc-IP) assay was used (Promega, Madison, Wis., USA, Cat. No. V9920). The assay makes use of a luminogenic isopropylacetal (IPA) substrate that is a derivative from beetle luciferin, a substrate of luciferase enzymes. The IPA substrate is converted by CYP3A4 to luciferin, which in turn reacts with luciferase to produce an amount of light that is directly proportional to the activity of CYP3A4. Compounds were serially diluted in DMSO and finally in 400 mM $K_2HPO_4$, pH 7.4. 5 µl of compound solution and 5 µl of CYP3A4/substrate solution were combined in the well of a white 384-well Optiplate (Perkin Elmer). The DMSO concentration in the assay was 0.1%. After incubation for 10 minutes at room temperature in the dark, 10 µl of NADPH regeneration system was added and incubation was continued for 10 min. Then, 20 µl of Luciferin Detection Reagent was added to stop the reaction, and incubation was continued for another 20 min. Luminescence was measured on an Envision multimode reader and $IC_{50}$ values were calculated using XLfit™. Concentrations of enzyme, substrate and other reagents were set according to the instructions of the manufacturer (Promega document TB325, revision 3/15). Instead of in a 96-well plate, the assay was performed in 384-well white Perkin Elmer Optiplate (cat. no. 6007290).

A similar assay was used to determine the inhibitory potency of compounds on CYP2D6. The P450-Glo CYP2D6 Luc-IP assay (Promega; Cat. No. V9890) makes use of a luminogenic substrate (ME EGE) that is converted to luciferin by CYP2D6. This assay was performed according to the instruction of the manufacturer (Promega document TB325, revision 3/15), with the difference that it was performed in a 384-well white Perkin Elmer Optiplates (cat. no. 6007290), instead of a 96-well plate. All volumes mentioned in the manufacturer's instruction were divided by a factor 2.5. The DMSO concentration during the incubation phase of the assay was 0.1%. The $IC_{50}$ values of all exemplified compounds were found to be higher than 5 µM in both assays. Compounds of examples 16, 23, 42, 43, 45, 46, 55, 57, 61, 62, 65, 66, 67, 68, 70, 71, 72, 74, 75, 81, 82, 91, 94, 102, 104, 106, 110, 117, 119, 122, 123, 124, 125, 126, 128, 130 and 135 showed an $IC_{50}$ value >5 µM and <10 µM for CYP3A4 and compounds of examples 1, 2, 3, 4, 5, 6, 7, 8, 9, 10, 12, 13, 14, 15, 17, 18, 19, 20, 21, 22, 24, 25, 26, 27, 28, 29, 30, 31, 32, 33, 34, 35, 36, 37, 38, 39, 40, 41, 44, 47, 48, 49, 50, 51, 52, 53, 54, 56, 58, 59, 60, 63, 64, 69, 73, 76, 77, 78, 79, 80, 83, 84, 85, 86, 87, 88, 89, 90, 92, 93, 95, 96, 97, 98, 99, 100, 101, 103, 105, 107, 108, 109, 111, 112, 113, 114, 115, 116, 118, 120, 121, 127, 129, 131, 132, 133, 134, 136, 137 and 138 showed an $IC_{50}$ of >10 µM for CYP3A4.

Compounds of examples 10, 14, 16, 57, 72, 85, 117, 126 and 128 showed an $IC_{50}$ value >5 µM and <10 µM for CYP2D6 and compounds of examples 1, 2, 3, 4, 5, 6, 7, 8, 9, 12, 13, 15, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 58, 59, 60, 61, 62, 63, 64, 65, 66, 67, 68, 69, 70, 71, 73, 74, 75, 76, 77, 78, 79, 80, 81, 82, 83, 84, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 118, 119, 120, 121, 122, 123, 124, 125, 127, 129, 130, 131, 132, 133, 134, 135, 136, 137 and 138 showed an $IC_{50}$ of >10 µM for CYP2D6.

The invention claimed is:
1. A compound of Formula I:

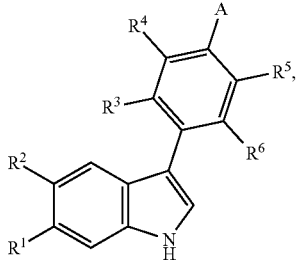

Formula I or a pharmaceutically acceptable salt thereof wherein,
$R^1$ is fluoro,
$R^2$ is hydrogen,
$R^3$ is selected from the group consisting of hydrogen and halogen,
$R^4$ is selected from the group consisting of hydrogen, halogen and (1-6C)alkoxy,
$R^5$ is selected from the group consisting of hydrogen and halogen,
$R^6$ is selected from the group consisting of hydrogen and halogen,
A is

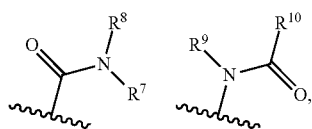

$R^7$ is selected from the group consisting of:
   a) hydroxy(1-6C)alkyl,
   b) di[(1-6C)alkyl]amino(1-6C)alkyl,
   c) (3-7C)cycloalkyl,
   d) (2-7C)heterocycloalkyl(2-3C)alkyl, and
   e) (2-7C)heterocycloalkyl,
$R^7$ optionally being substituted with one or more groups selected from the group consisting of halogen, hydroxyl, amino, cyano, hydroxy(1-6C)alkyl, di[(1-6C)alkyl]amino(1-6C)alkyl, (6-10C)aryl, (3-7C)cycloalkyl, (1-6C)alkyl, (1-6C)alkylcarbonyl, aminosulfonyl, and (1-6C)alkoxy, and
$R^8$ is hydrogen.

2. The compound according to claim 1 wherein $R^6$ is hydrogen.
3. The compound according to claim 1 wherein $R^3$ is selected from the group consisting of hydrogen and fluoro.
4. The compound according to claim 1 wherein $R^5$ is selected from the group consisting of hydrogen and fluoro.
5. The compound according to claim 1 wherein $R^4$ is selected from the group consisting of hydrogen, fluoro, chloro and methoxy.
6. The compound according to claim 1 wherein A is

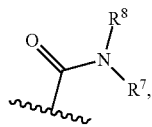

$R^7$ is selected from the group consisting of:
   a) hydroxy(1-6C)alkyl,
   b) di[(1-6C)alkyl]amino(1-6C)alkyl,
   c) (2-7C)heterocycloalkyl(3C)alkyl, and
   d) (2-7C)heterocycloalkyl,
$R^7$ optionally being substituted with one or more groups selected from fluoro and (1-6C)alkyl, and, and
$R^8$ is hydrogen.

7. A pharmaceutical composition comprising a compound of Formula I or a pharmaceutically acceptable salt thereof according to claim 1, and one or more pharmaceutically acceptable excipients.
8. The pharmaceutical composition according to claim 7, further comprising at least one therapeutically active agent.
9. A compound or a pharmaceutically acceptable salt, wherein the compound is selected from compounds of the group consisting of:
N-[2-(dimethylamino)-1-methyl-ethyl]-4-(6-fluoro-1H-indol-3-yl)benzamide,
4-(6-Fluoro-1H-indol-3-yl)-N-isopropyl-benzamide,
4-(6-Fluoro-1H-indol-3-yl)-N-[(1S)-1-(hydroxymethyl)-2-methyl-propyl]benzamide,
N-[3-(dimethylamino)propyl]-4-(6-fluoro-1H-indol-3-yl)benzamide,
4-(6-Fluoro-1H-indol-3-yl)-N-(2-hydroxyethyl)benzamide,
N-(1-cyanocyclopropyl)-4-(6-fluoro-1H-indol-3-yl)benzamide,
4-(6-Fluoro-1H-indol-3-yl)-N-(2-hydroxy-2-methyl-propyl)benzamide,
4-(6-fluoro-1H-indol-3-yl)-N-[(1R)-2-hydroxy-1-methyl-ethyl]benzamide,
4-(6-fluoro-1H-indol-3-yl)-N-[(1S)-2-hydroxy-1-methyl-ethyl]benzamide,
4-(6-fluoro-1H-indol-3-yl)-N-[(1R)-2-hydroxy-1-phenyl-ethyl]benzamide,
4-(6-Fluoro-1H-indol-3-yl)-N-[(1R)-2-methoxy-1-methyl-ethyl]benzamide,
4-(6-Fluoro-1H-indol-3-yl)-N-[(3S)-3-piperidyl]benzamide,
4-(6-Fluoro-1H-indol-3-yl)-N-[(3S)-quinuclidin-3-yl]benzamide,
4-(6-Fluoro-1H-indol-3-yl)-N-(2-hydroxy-1-methyl-propyl)benzamide,
N-[2-(diethylamino)-1-methyl-ethyl]-4-(6-fluoro-1H-indol-3-yl)benzamide,
4-(6-Fluoro-1H-indol-3-yl)-N-(1-methyl-4-piperidyl)benzamide,
4-(6-Fluoro-1H-indol-3-yl)-N-(1-methyl-3-piperidyl)benzamide,
4-(6-Fluoro-1H-indol-3-yl)-N-(oxetan-3-yl)benzamide,
4-(6-Fluoro-1H-indol-3-yl)-N-[(3R)-3-piperidyl]benzamide,
4-(6-Fluoro-1H-indol-3-yl)-N-[[(3R)-3-piperidyl]methyl]benzamide,
4-(6-Fluoro-1H-indol-3-yl)-N-[(3S,4R)-3-methoxy-4-piperidyl]benzamide,
4-(6-Fluoro-1H-indol-3-yl)-N-tetrahydropyran-4-yl-benzamide,
4-(6-Fluoro-1H-indol-3-yl)-N-[(1S)-1-([1,2,4]triazolo[4,3-a]pyridin-3-yl)ethyl]benzamide,
4-(6-Fluoro-1H-indol-3-yl)-N-[2-(1-piperidyl)ethyl]benzamide,
4-(6-Fluoro-1H-indol-3-yl)-N-(8-methyl-8-azabicyclo[3.2.1]octan-3-yl)benzamide,
4-(6-Fluoro-1H-indol-3-yl)-N-[2-hydroxy-1-(hydroxymethyl)-1-methyl-ethyl]benzamide, N-[(1S)-1,2-dimethylpropyl]-4-(6-fluoro-1H-indol-3-yl)benzamide,
4-(6-Fluoro-1H-indol-3-yl)-N-[(1R,2R)-2-hydroxycyclohexyl]benzamide,
2-Chloro-4-(6-fluoro-1H-indol-3-yl)-N-[(1R)-2-hydroxy-1-methyl-ethyl]benzamide,
2-Chloro-N-[3-(dimethylamino)propyl]-4-(6-fluoro-1H-indol-3-yl)benzamide,
2-Chloro-4-(6-fluoro-1H-indol-3-yl)-N-(2,2,2-trifluoroethyl)benzamide,
2-Chloro-4-(6-fluoro-1H-indol-3-yl)-N-[(1S)-2-hydroxy-1-methyl-ethyl]benzamide,
2-Chloro-4-(6-fluoro-1H-indol-3-yl)-N-[(3S)-3-piperidyl]benzamide,
2,6-Difluoro-4-(6-fluoro-1H-indol-3-yl)-N-[(1R)-2-hydroxy-1-methyl-ethyl]benzamide,
2,6-Difluoro-4-(6-fluoro-1H-indol-3-yl)-N-(2,2,2-trifluoroethyl)benzamide,
2,6-Difluoro-4-(6-fluoro-1H-indol-3-yl)-N-[(3S)-3-piperidyl]benzamide,
N-[3-(dimethylamino)propyl]-2,6-difluoro-4-(6-fluoro-1H-indol-3-yl)benzamide,
2,6-Difluoro-4-(6-fluoro-1H-indol-3-yl)-N-[(1S)-2-hydroxy-1-methyl-ethyl]benzamide,
N-(cis-4-aminocyclohexyl)-4-(6-fluoro-1H-indol-3-yl)benzamide,
4-(6-Fluoro-1H-indol-3-yl)-N-[(1-hydroxycyclobutyl)methyl]benzamide,
4-(6-Fluoro-1H-indol-3-yl)-N-[(4-hydroxy-1-methyl-4-piperidyl)methyl]benzamide,
4-(6-Fluoro-1H-indol-3-yl)-N-[(1R,5S)-3-oxabicyclo[3.1.0]hexan-6-yl]benzamide,
N-[(2S)-2,3-dihydroxypropoxy]-4-(6-fluoro-1H-indol-3-yl)benzamide,
2-Chloro-4-(6-fluoro-1H-indol-3-yl)-N-(1-methyl-3-piperidyl)benzamide,
2-Chloro-4-(6-fluoro-1H-indol-3-yl)-N-(1-methyl-4-piperidyl)benzamide,
2-Chloro-4-(6-fluoro-1H-indol-3-yl)-N-(2-pyrrolidin-1-ylethyl)benzamide,
2-Chloro-4-(6-fluoro-1H-indol-3-yl)-N-[3-(4-methylpiperazin-1-yl)propyl]benzamide,
2-Chloro-N-[2-(diethylamino)-1-methyl-ethyl]-4-(6-fluoro-1H-indol-3-yl)benzamide,
4-(6-Fluoro-1H-indol-3-yl)-N-[(3S,4R)-3-fluoro-4-piperidyl]benzamide,
4-(6-Fluoro-1H-indol-3-yl)-2-methoxy-N-[(3S)-3-piperidyl]benzamide,
4-(6-Fluoro-1H-indol-3-yl)-N-[(4-fluoro-4-piperidyl)methyl]benzamide,
4-(6-Fluoro-1H-indol-3-yl)-N-(2-pyrrolidin-1-ylethyl)benzamide,
N-[3-(dimethylamino)-2-hydroxy-propyl]-4-(6-fluoro-1H-indol-3-yl)benzamide
N-[2-(diethylamino)-1-methyl-ethyl]-4-(6-fluoro-1H-indol-3-yl)-2-methoxy-benzamide,
N-(2-diethylaminoethyl)-4-(6-fluoro-1H-indol-3-yl)benzamide,
2-Chloro-N-[2-(dimethylamino)-1-methyl-ethyl]-4-(6-fluoro-1H-indol-3-yl)benzamide,
N-(azepan-4-yl)-4-(6-fluoro-1H-indol-3-yl)benzamide,
4-(6-Fluoro-1H-indol-3-yl)-N-[[(2S)-pyrrolidin-2-yl]methyl]benzamide,
N-cyclopropyl-4-(6-fluoro-1H-indol-3-yl)benzamide,
4-(6-Fluoro-1H-indol-3-yl)-N-[(1S,2S)-2-hydroxycyclopentyl]benzamide,
4-(6-Fluoro-1H-indol-3-yl)-N-morpholino-benzamide,
4-(6-Fluoro-1H-indol-3-yl)-N-[[(3S)-3-piperidyl]methyl]benzamide,
4-(6-Fluoro-1H-indol-3-yl)-N-[[(3R)-pyrrolidin-3-yl]methyl]benzamide,
4-(6-Fluoro-1H-indol-3-yl)-N-[(1R)-2-hydroxy-1-methyl-ethyl]-2-methoxy-benzamide,
N-(2-amino-2-oxo-ethyl)-4-(6-fluoro-1H-indol-3-yl)benzamide,
N-(3,3-difluorocyclobutyl)-4-(6-fluoro-1H-indol-3-yl)benzamide,
2-Chloro-N-[2-[(3S,4S)-3,4-dihydroxypyrrolidin-1-yl]ethyl]-4-(6-fluoro-1H-indol-3-yl)benzamide,
2-Chloro-N-[2-[(3R,4R)-3,4-dihydroxypyrrolidin-1-yl]ethyl]-4-(6-fluoro-1H-indol-3-yl)benzamide,
3-Fluoro-4-(6-fluoro-1H-indol-3-yl)-N-[(1R)-2-hydroxy-1-methyl-ethyl]benzamide,
4-(6-Fluoro-1H-indol-3-yl)-N-(3-piperidyl)benzamide,
N-(1-acetyl-3-piperidyl)-4-(6-fluoro-1H-indol-3-yl)benzamide,
Methyl 2-[[4-(6-fluoro-1H-indol-3-yl)benzoyl]amino]-2-(4-piperidyl)acetate,
2-Fluoro-4-(6-fluoro-1H-indol-3-yl)-N-[(1S)-2-hydroxy-1-methyl-ethyl]benzamide,
N-[3-(dimethylamino)propyl]-2-fluoro-4-(6-fluoro-1H-indol-3-yl)benzamide,
2-Fluoro-4-(6-fluoro-1H-indol-3-yl)-N-[(3S)-3-piperidyl]benzamide,
N-[3-(dimethylamino)propyl]-4-(6-fluoro-1H-indol-3-yl)-3-methyl-benzamide,
2-Fluoro-4-(6-fluoro-1H-indol-3-yl)-N-[(1R)-2-hydroxy-1-methyl-ethyl]benzamide,
4-(6-Fluoro-1H-indol-3-yl)-N-(1-sulfamoyl-3-piperidyl)benzamide,
4-(6-Fluoro-1H-indol-3-yl)-N-[(3R)-quinuclidin-3-yl]benzamide,
4-(6-Fluoro-1H-indol-3-yl)-N-(3,3,3-trifluoropropyl)benzamide,
4-(6-Fluoro-1H-indol-3-yl)-N-[3-(4-methylpiperazin-1-yl)propyl]benzamide,
4-(6-Fluoro-1H-indol-3-yl)-N-[(1S)-2-hydroxy-1-methyl-ethyl]-2-methoxy-benzamide, and
N-[3-(dimethylamino)propyl]-4-(6-fluoro-1H-indol-3-yl)-2-methoxy-benzamide, and
the pharmaceutically acceptable salt is selected from the group consisting of pharmaceutically acceptable salts of said compounds.

10. A compound or a pharmaceutical acceptable salt, wherein the compound is selected from compounds of the group consisting of:
N-[2-(dimethylamino)-1-methyl-ethyl]-4-(6-fluoro-1H-indol-3-yl)benzamide,
4-(6-Fluoro-1H-indol-3-yl)-N-isopropyl-benzamide,
N-[3-(dimethylamino)propyl]-4-(6-fluoro-1H-indol-3-yl)benzamide,
4-(6-fluoro-1H-indol-3-yl)-N-[(1S)-2-hydroxy-1-methyl-ethyl]benzamide,
4-(6-Fluoro-1H-indol-3-yl)-N-[(3S)-3-piperidyl]benzamide,
4-(6-Fluoro-1H-indol-3-yl)-N-[(3S)-quinuclidin-3-yl]benzamide,
4-(6-Fluoro-1H-indol-3-yl)-N-(2-hydroxy-1-methyl-propyl)benzamide,
N-[2-(diethylamino)-1-methyl-ethyl]-4-(6-fluoro-1H-indol-3-yl)benzamide,
4-(6-Fluoro-1H-indol-3-yl)-N-(1-methyl-4-piperidyl)benzamide, 4-(6-Fluoro-1H-indol-3-yl)-N-(1-methyl-3-piperidyl)benzamide,
2-Chloro-N-[3-(dimethylamino)propyl]-4-(6-fluoro-1H-indol-3-yl)benzamide,
2-Chloro-4-(6-fluoro-1H-indol-3-yl)-N-[(1S)-2-hydroxy-1-methyl-ethyl]benzamide,
2-Chloro-4-(6-fluoro-1H-indol-3-yl)-N-[(3S)-3-piperidyl]benzamide,
2,6-Difluoro-4-(6-fluoro-1H-indol-3-yl)-N-[(3S)-3-piperidyl]benzamide,
2-Chloro-4-(6-fluoro-1H-indol-3-yl)-N-(1-methyl-3-piperidyl)benzamide,
2-Chloro-4-(6-fluoro-1H-indol-3-yl)-N-(1-methyl-4-piperidyl)benzamide,
2-Chloro-4-(6-fluoro-1H-indol-3-yl)-N-(2-pyrrolidin-1-ylethyl)benzamide,
2-Chloro-4-(6-fluoro-1H-indol-3-yl)-N-[3-(4-methylpiperazin-1-yl)propyl]benzamide,
2-Chloro-N-[2-(diethylamino)-1-methyl-ethyl]-4-(6-fluoro-1H-indol-3-yl)benzamide,
4-(6-Fluoro-1H-indol-3-yl)-N-[(3S,4R)-3-fluoro-4-piperidyl]benzamide,
4-(6-Fluoro-1H-indol-3-yl)-2-methoxy-N-[(3S)-3-piperidyl]benzamide,
4-(6-Fluoro-1H-indol-3-yl)-N-[(4-fluoro-4-piperidyl)methyl]benzamide,
4-(6-Fluoro-1H-indol-3-yl)-N-(2-pyrrolidin-1-ylethyl)benzamide,
N-[3-(dimethylamino)-2-hydroxy-propyl]-4-(6-fluoro-1H-indol-3-yl)benzamide,
N-[2-(diethylamino)-1-methyl-ethyl]-4-(6-fluoro-1H-indol-3-yl)-2-methoxy-benzamide,
N-(2-diethylaminoethyl)-4-(6-fluoro-1H-indol-3-yl)benzamide,
2-Chloro-N-[2-(dimethylamino)-1-methyl-ethyl]-4-(6-fluoro-1H-indol-3-yl)benzamide,
N-(azepan-4-yl)-4-(6-fluoro-1H-indol-3-yl)benzamide,
4-(6-Fluoro-1H-indol-3-yl)-N-[[(2S)-pyrrolidin-2-yl]methyl]benzamide,
4-(6-Fluoro-1H-indol-3-yl)-N-(3-piperidyl)benzamide,
2-Fluoro-4-(6-fluoro-1H-indol-3-yl)-N-[(1S)-2-hydroxy-1-methyl-ethyl]benzamide,
N-[3-(dimethylamino)propyl]-2-fluoro-4-(6-fluoro-1H-indol-3-yl)benzamide,
2-Fluoro-4-(6-fluoro-1H-indol-3-yl)-N-[(3S)-3-piperidyl]benzamide,
4-(6-Fluoro-1H-indol-3-yl)-N-[(3R)-quinuclidin-3-yl]benzamide,
4-(6-Fluoro-1H-indol-3-yl)-N-(3,3,3-trifluoropropyl)benzamide,
4-(6-Fluoro-1H-indol-3-yl)-N-[3-(4-methylpiperazin-1-yl)propyl]benzamide, and
N-[3-(dimethylamino)propyl]-4-(6-fluoro-1H-indol-3-yl)-2-methoxy-benzamide, and
the pharmaceutically acceptable salt is selected from the group consisting of pharmaceutically acceptable salts of said compounds.

* * * * *